US008609885B2

(12) United States Patent
Malofsky et al.

(10) Patent No.: US 8,609,885 B2
(45) Date of Patent: Dec. 17, 2013

(54) SYNTHESIS OF METHYLENE MALONATES SUBSTANTIALLY FREE OF IMPURITIES

(75) Inventors: Adam G. Malofsky, Loveland, OH (US); Tanmoy Dey, Stamford, CT (US); Jeffrey M. Sullivan, Goshen, OH (US); Yangbin Chen, Lima, NY (US); Stanley C. Wojciak, New Britain, CT (US); Bernard M. Malofsky, Bloomfield, CT (US)

(73) Assignee: Bioformix Inc., Loveland, OH (US)

( * ) Notice: Subject to any disclaimer, the term of this patent is extended or adjusted under 35 U.S.C. 154(b) by 0 days.

(21) Appl. No.: 13/880,438

(22) PCT Filed: Oct. 19, 2011

(86) PCT No.: PCT/US2011/056903
§ 371 (c)(1),
(2), (4) Date: Jul. 22, 2013

(87) PCT Pub. No.: WO2012/054616
PCT Pub. Date: Apr. 26, 2012

(65) Prior Publication Data
US 2013/0303719 A1     Nov. 14, 2013

Related U.S. Application Data

(60) Provisional application No. 61/405,056, filed on Oct. 20, 2010, provisional application No. 61/405,049, filed on Oct. 20, 2010, provisional application No. 61/405,033, filed on Oct. 20, 2010, provisional application No. 61/405,029, filed on Oct. 20, 2010, provisional application No. 61/405,078, filed on Oct. 20, 2010, provisional application No. 61/523,311, filed on Aug. 13, 2011, provisional application No. 61/523,705, filed on Aug. 15, 2011.

(51) Int. Cl.
*C07C 69/34*     (2006.01)

(52) U.S. Cl.
USPC .......................................................... 560/190

(58) Field of Classification Search
USPC ................................................. 560/190, 191
See application file for complete search history.

(56) References Cited

U.S. PATENT DOCUMENTS

| 2,313,501 A | 3/1943 | Bryant |
| 2,330,033 A | 9/1943 | D'Alello |

(Continued)

FOREIGN PATENT DOCUMENTS

WO    WO 2012/054633     4/2012

OTHER PUBLICATIONS

M. Ware et al.: "DBU: An Efficient Catalyst for Knoeveganel Condensation under Solvent-free Condition," Bulletin of the Catalysis Society of India, (2007), vol. 6, pp. 104-106.

(Continued)

*Primary Examiner* — Wu-Cheng Winston Shen
*Assistant Examiner* — Blaine G Doletski
(74) *Attorney, Agent, or Firm* — Edwards Wildman Palmer LLP; Barry Kramer; Nicholas J. DiCeglie, Jr.

(57) ABSTRACT

The present invention provides improved methods for the chemical synthesis of methylene malonates using the Knovenagel synthesis reaction. The method of the invention provides for improved methylene malonates by significantly reducing or eliminating the formation of alternative and/or deleterious side products, significantly reducing or eliminating unwanted consumption of methylene malonates, and significantly reducing or eliminating the degradation of methylene malonates. These advantages result in methylene malonates, which upon recovery, are of higher quality, greater purity, improved yield and possess overall improved performance characteristics (e.g., improved cure speed, retention of cure speed, improved shelf-life and/or stability).

10 Claims, 20 Drawing Sheets

(56) References Cited

U.S. PATENT DOCUMENTS

| | | | |
|---|---|---|---|
| 3,197,318 | A | 7/1965 | Jack |
| 3,221,745 | A | 12/1965 | Coover, Jr. |
| 3,523,097 | A | 8/1970 | Coover, Jr. |
| 3,557,185 | A | 1/1971 | Ito |
| 3,975,422 | A | 8/1976 | Buck |
| 4,049,698 | A | 9/1977 | Hawkins et al. |
| 4,056,543 | A | 11/1977 | Ponticello |
| 4,160,864 | A | 7/1979 | Ponticello et al. |
| 4,931,584 | A | 6/1990 | Bru-Magniez et al. |
| 5,142,098 | A * | 8/1992 | Bru-Magniez et al. ......... 560/80 |
| 5,550,172 | A | 8/1996 | Regula et al. |
| 6,106,807 | A | 8/2000 | Albayrak et al. |
| 6,211,273 | B1 | 4/2001 | Bru-Magniez et al. |
| 6,245,933 | B1 | 6/2001 | Malofsky et al. |
| 6,420,468 | B2 | 7/2002 | Bru-Magniez et al. |
| 6,440,461 | B1 | 8/2002 | Bru-Magniez et al. |
| 6,512,023 | B1 | 1/2003 | Malofsky et al. |
| 6,610,078 | B1 | 8/2003 | Bru-Magniez et al. |
| 6,699,928 | B2 | 3/2004 | Cobbley et al. |
| 6,750,298 | B1 | 6/2004 | Bru-Magniez et al. |
| 2004/0076601 | A1 | 4/2004 | Bru-Magniez et al. |
| 2008/0227919 | A9 | 9/2008 | Li et al. |

OTHER PUBLICATIONS

V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.

J. S. Yadav et al.,: "Phosphane-Catalyzed Knoevenagel Condensation: a Facile Synthesis of α-Cyanoacrylates and α-Cyanoacrylonitriles," Eur. J. Org. Chem. (2004), pp. 546-551.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org. Chem., (2006), pp. 3767-3770.

H. A. Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

B. M. Reddy et al.: "An Easy-to-use Heterogeneous Promoted Zirconia Catalyst for Knoevenagel Condensation in liquid Phase under Solvent-Free Conditions," Journal of Molecular Catalysis A: Chemical, (2006), vol. 258, pp. 302-307.

D. H. Jung et al.: "New and General Methods for the Synthesis of Arylmethylene Bis(3-Hydroxy-2-Cyclohexene-1-Ones) and Xanthenediones by EDDA and in(OTf)3-Catalyzed One-Pot Domino Knoevenagel/Michael or Koevenagel/Michael/ Cyclodehydration Reactions," Bull. Korean Chem. Soc. (2009) vol. 30, No. 9, pp. 1989-1995.

P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.

P. Klemarwczyk: "A General Synthesis of 1,1 Disubstituted Electron Deficient Olefins and their Polymer Properties," Polymer, (1998), vol. 39, No. 1, pp. 173-181.

C. Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Aurangabad 431 004 (MS), India, (n/a), pp. n/a.

P. Ballesteros et al.: "DI-*tert*-Butyl Methylenemalonate [Propanedioic Acid, Methylene-, bis(1,1-dimethylethyl)ester]," Organic Syntheses. Coll. (1990), vol. 7, p. 142 ; (1986) vol. 64, p. 63.

A. M. Vetrova et al.: "Improvement of the Thermal Stability of Cyanoacrylate Adhesives," Polymer Science, Series D, (2009), vol. 2, No. 1, pp. 27-30.

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

G. Lai et al.: "Ionic Liquid Functionalized Silica Gel: Novel Catalyst and Fixed Solvent," Tetrahedron Letters (2006), vol. 47, pp. 6951-6953.

J. R. Harjani et al.: "Lewis Acidic Ionic Liquids for the Synthesis of Electrophilic Alkenes via the Knoevenagel Condensation," Tetrahedron Letters, (2002), vol. 43, pp. 1127-1130.

Ballesteros et al.: "Synthesis of DI-*tert*-Butyl Methylenemalonate, a Sterically Hindered 1,1-Dicarbonyl Alkene," J. Org. Chem, (1983), vol. 48, pp. 3603-3605.

T. Doi et al.: "Synthesis of Dimethyl gloiosiphne A by Way of Palladium-Catalyzed Domino Cyclization," J. Org. Chem., (2007), vol. 72, pp. 3667-3671.

\* cited by examiner

SYNTHESIS OF METHYLENE MALONATES SUBSTANTIALLY FREE OF IMPURITIES

CROSS REFERENCE TO RELATED APPLICATIONS

This application is a U.S. National Stage application under 35 U.S.C. §371 of International Patent Application Serial No. PCT/US2011/056903, filed Oct. 19, 2011, which Application claims the benefit of priority of U.S. Provisional Patent Application No. 61/405,029, filed Oct. 20, 2010, U.S. Provisional Patent Application No. 61/405,049, filed Oct. 20, 2010, U.S. Provisional Patent Application No. 61/405,078, filed Oct. 20, 2010, U.S. Provisional Patent Application No. 61/405,033, filed Oct. 20, 2010, U.S. Provisional Patent Application No. 61/405,056, filed Oct. 20, 2010, U.S. Provisional Patent Application No. 61/523,311, filed Aug. 13, 2011, and U.S. Provisional Patent Application No. 61/523,705, filed Aug. 15, 2011, the disclosures of each of which are expressly incorporated by reference in their entireties.

INCORPORATION BY REFERENCE

This application claims priority to U.S. Provisional Application Ser. Nos. 61/405,029, filed Oct. 20, 2010, 61/405,033, filed Oct. 20, 2010, 61/405,049, filed Oct. 20, 2010, 61/405,056, filed Oct. 20, 2010, 61/405,078, filed Oct. 20, 2010, 61/523,311, filed Aug. 13, 2011, and 61/523,705, filed Aug. 15, 2011, the entire contents each of which are incorporated herein by reference in their entireties.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The invention relates to improved methods for producing methylene malonate monomers and to the use and/or application of methylene malonate monomers prepared by the methods of the invention as commercial products and compositions, including, for example, monomer-based products (e.g., inks, adhesives, coatings, sealants or reactive molding) and polymer-based products (e.g., fibers, films, sheets, medical polymers, composite polymers and surfactants).

2. Background

Methylene malonates are compounds having the general formula (I):

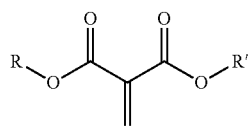

(I)

wherein R and R' may be the same or different and may represent nearly any substituent or side-chain. Such compounds have been known since 1886 where the formation of diethyl methylene malonate was first demonstrated by W. H. Perkin, Jr. (Perkin, Ber. 19, 1053 (1886)).

These compounds have the potential to form the basis of a highly valuable novel large-scale platform for the chemical synthesis of a new order of raw materials for the generation of a wide variety of new chemical products, including inks, adhesives, coatings, sealants, molding, fibers, films, sheets, medical polymers, composites, surfactants and the like. While the potential is there for such materials, methylene malonates or materials made therefrom have found very limited commercial success owing to the difficulty of their production, including poor and erratic yields, lack of reactivity, and general instability of the monomer products. These difficulties stem from the deficiencies in the methods developed over the years which have proposed various schemes for synthesizing methylene malonates.

However, while such earlier methods for producing methylene malonates have been known for many years, these prior methods suffer significant deficiencies which preclude their use in obtaining commercially viable monomers. Such deficiencies include unwanted polymerization of the monomers during synthesis (e.g., formation of polymers or oligomers or alternative complexes), formation of undesirable side products (e.g., ketals or other latent acid-forming species which impede rapid polymerization), degradation of the product, insufficient and/or low yields, and ineffective and/or poorly functioning monomer product (e.g., poor adhesive characteristics, stability, or other functional characteristics), among other problems. The overall poorer yield, quality, and chemical performance of the monomer products formed by prior methods has impinged on their practical use in the production of the above commercial and industrial products. No viable solutions to solve the aforementioned problems have yet been proposed, accepted and/or recognized and certainly do not exist currently in the industry.

For example, in U.S. Pat. No. 2,330,033 to Gaetano D'Alelio ("the '033 patent"), methylene malonic esters are prepared by condensing a malonic ester with formaldehyde under alkaline conditions, acidifying with acetic acid and dehydrating the mass and distilling the methylene malonic ester. In each example of the '033 patent, the condensation reaction is acidified using acetic acid. Furthermore, the ester is described as polymerizing spontaneously in the absence of inhibitors. Thus, the reaction conditions described in the '033 patent would have led to the undesirable premature polymerization of the monomer and the production of deleterious side products. Further, the reference does not even recognize the formation of such deleterious side products, let alone does it provide any teachings or suggestions as to how to avoid or eliminate the formation of these impurities. Accordingly, the methylene malonates purportedly formed by this process are impractical for use in the production of viable commercial and industrial products.

Similarly, in U.S. Pat. No. 2,313,501 to Bachman et al. ("the '501 patent"), methylene dialkyl malonates are prepared by the reaction of dialkyl malonates with formaldehyde in the presence of an alkali metal salt of a carboxylic acid in a substantially anhydrous carboxylic acid solvent. The method of the '501 patent purports to provide higher yields than the prior methods of condensing formaldehyde with a dialkyl malonate in the presence of a base. In the '501 patent, methylene diethyl malonate is distilled directly from the reaction mixture under sub-atmospheric pressure. The ester is described as forming a soft waxy white polymer upon standing, indicating the presence of a high degree of deleterious side products. The '501 patent does not even recognize the formation of such deleterious side products, let alone does it provide any teachings or suggestions as to how to avoid or eliminate the formation of such impurities. Thus, the methylene malonates purportedly formed by this process are highly unstable and are impractical for use in the production of viable commercial and industrial products.

Furthermore, in U.S. Pat. No. 3,197,318 to Halpern et al. ("the '318 patent"), dialkyl methylene malonic acid esters are prepared by condensing dimethylmalonate with formaldehyde in the presence of acetic acid and an acetate of a heavy metal at 100-110° C. The reaction mixture is directly distilled under reduced pressure. The '318 patent states that in the anhydrous composition, the reaction either fails to occur or is greatly delayed by the inhibitor up to the time when the effectiveness of the inhibitor is reduced by contact of moisture therewith (from occluded surface water on glass, metal or the like). The unfavorable reaction conditions described in this reference would have led to the production of deleterious side products. The '318 patent does not even recognize the formation or presence of these impurities, let alone offer teachings or suggestions as to how to avoid or eliminate their formation. Accordingly, the methylene malonates purportedly formed by the process of the '318 patent would have been impractical for their use in the production of viable commercial products.

Also, in U.S. Pat. No. 3,221,745 to Coover et al. ("the '745 patent"), monomeric dialkyl esters of methylene malonic acid are purportedly prepared in high purity because even with small amounts of impurities that influence polymerization the adhesive utility will be impaired. The '745 patent describes removing all impurities to levels below 100 parts-per-million preferably below 10 parts-per-million. The monomers are prepared by hydrogenating the olefinic bond of a dialkyl alkoxy-methylenemalonate in the presence of a hydrogenation catalyst and pyrolyzing the reaction product. The '745 patent states that these high purity materials polymerize and form firm bonds in situ rapidly, within seconds. Indeed, the '745 patent, like related U.S. Pat. No. 3,523,097 to Coover et al. ("the '097 patent"), requires the use of an acidic stabilizer to enhance shelf-life and to prevent premature polymerization. However, the high temperature conditions of the pyrolysis reaction invariably results in the formation of unwanted and deleterious side products and is a much more expensive and difficult synthesis process for preparing methylene malonate as compared to the Knovenagel reaction with formaldehyde. Thus, the monomer purportedly formed by the processes of the '745 and '097 patents is impractical for use in the production of viable commercial and industrial products.

Still further, in U.S. Pat. No. 3,758,550 to Eck et al. ("the '550 patent") report on a general process for producing methylene malonic esters of the general formula $CH_2=C(CO_2R)_2$, by reacting paraformaldehyde in glacial acetic acid in the presence of a catalyst to form a product in the form of a "gel" which is then "cracked" at high temperature distillation. The reaction is conducted over long periods of time, including up to 15 hours, and produces a substantial amount of deleterious side products, as evidenced by the gelatinous characteristics of the product. Further, the '550 patent contains no support showing the functionality of the monomers produced. Due to the likely presence of high levels of impurities, the functionality of the monomers produced by the '550 patent would likely be substantially compromised.

Citing numerous disadvantages of the foregoing processes, which disadvantages were said to make them difficult, if not impossible, to provide commercially viable monomers, Bru-Magniez et. al. (U.S. Pat. No. 4,932,584 and U.S. Pat. No. 5,142,098) ("the '584 and '098 patents") developed a process whereby anthracene adducts were prepared by reacting mono- or di-malonic acid ester with formaldehyde in the presence of anthracene, most preferably in a non-aqueous solvent medium in the presence of select catalysts. According to these patents, the anthracene adducts were said to be readily produced in high yields with the desired methylene malonates obtained by stripping them from the anthracene adduct by any of the known methods including heat treatment, thermolysis, pyrolysis or hydrolysis; preferably heat treatment in the presence of maleic anhydride. The resultant crude products were then subjected to multiple distillations, preferably lower temperature distillations under vacuum, to recover the purified methylene malonates. Despite the claim to high yields, their crude yields were generally in the range of 21-71%, and more importantly, nothing is taught with respect to the purity of the material obtained.

While the use of intermediate adducts promoted higher yields and allowed greater versatility, particularly with respect to the broader variety of methylene malonates capable of being produced, lingering problems persisted, namely batch-to-batch inconsistency and the general instability of the process as well as the so-formed crude and final products, especially in bulk storage, and of formulated products, such as adhesives, made with the same. Additionally, the adduct routes involve considerable added expense, particularly in light of the need for the additional reactants and other materials, added production steps and time, new energy requirements and environmental concerns, and the like. Furthermore, despite their advances, these processes have yet to fully or even adequately address, particularly from a commercial viability standpoint, the underlying and critical problems evidenced by the continuing inconsistency in the production of the methylidene malonates, particularly as reflected by the ongoing instability of the reaction mix particularly during the distillation and recovery of the desired product as well as of the recovered product. It is this erratic nature of the production process and resultant product and the attendant costs associated therewith that compromises and overshadows the commercial value and opportunity for these products.

Similar conclusions may be drawn from other representative prior references that purport to teach the synthesis of methylene malonates, including, for example, U.S. Pat. Nos. 3,557,185; 3,975,422; 4,049,698; 4,056,543; 4,160,864; and 6,106,807. None of these references, however, recognize the same problems discussed above, including the formation of deleterious side products, such as, ketals and other latent acid-forming species which impede monomer performance, the occurrence of unwanted polymerization (e.g., unintended formation of polymers, oligomers or alternative complexes) and the general degradation and instability of the monomer products which together substantially impedes the production of high-quality methylene malonate monomers having commercial viability.

In view of the above art, there remains no known single viable commercially suitable method or process for the chemical synthesis of methylene malonate monomers which may be utilized to produce these important raw materials for the generation of a wide variety of commercial and industrial products. Thus, a need exists for improved methods for synthesizing methylene malonate monomers that are capable of being viably used in commercial and industrial applications.

The present invention solves the aforementioned problems in the synthesis of methylene malonate monomers and paves the way to a commercially viable source of an important raw material.

SUMMARY OF THE INVENTION

The purpose and advantages of the present invention will be set forth in and apparent from the description that follows.

Additional advantages of the invention will be realized and attained by the methods and systems particularly pointed out in the written description and claims hereof, as well as from the appended drawings.

In one aspect, the present invention relates to a method of making a methylene malonate monomer comprising: (a) reacting a malonic acid ester with a source of formaldehyde in the presence of a basic catalyst and optionally in the presence of a non-acidic solvent, to form a reaction complex; and (b) recovering methylene malonate monomer from the reaction complex.

In another aspect, the present invention relates to a method of making a methylene malonate monomer comprising: (a) reacting a malonic acid ester with a source of formaldehyde in the presence of an acidic catalyst and optionally in the presence of an acidic or non-acidic solvent to form a reaction complex; and (b) recovering methylene malonate monomer from the reaction complex.

In yet another aspect, the present invention relates to a method of making a methylene malonate monomer comprising: (a) reacting a malonic acid ester with a source of formaldehyde in the presence of an acidic or basic catalyst and optionally in the presence of an acidic or non-acidic solvent, to form a reaction complex; (b) inactivating the catalyst; and (c) recovering methylene malonate monomer from the reaction complex.

In still another aspect, the present invention relates to a method of making a methylene malonate monomer comprising: (a) reacting a malonic acid ester with a source of formaldehyde in the presence of an acidic or basic catalyst and optionally in the presence of an acidic or non-acidic solvent, to form a reaction complex; (b) recovering the methylene malonate monomer the reaction complex; and (c) minimizing the recovery of volatile latent acid forming impurities from the reaction complex.

In various embodiments, the methods of the invention may further comprise the step of inactivating the catalyst. The step of inactivating the catalyst may comprise, but is not limited to, forming an insoluble precipitate of the catalyst and removing the precipitate from the reaction mixture.

When inactivating the catalyst, the precipitate may be formed in certain embodiments by the addition of sulfuric acid phosphoric acid or a combination thereof. In certain other embodiments, the precipitate is formed by reducing the solubility of the catalyst in the reaction mixture.

In aspects where the method of the invention includes the step of minimizing the recovery of volatile latent acid forming impurities, this step may in certain embodiments comprise (a) adding to the reaction mixture water and an acid having a pKa range of −8 to 5; (b) adding to the reaction mixture a sterically hindered organic acid; or (c) adding to the reaction mixture a non-volatile organic acid, or any combination of (a), (b) or (c).

In certain other embodiments, the step of minimizing the recovery of volatile latent acid forming impurities may comprise adding to the reaction mixture water and an acid having a pKa range of −8 to 5.

In aspects where the method of the invention involves a basic catalyst, the basic catalyst may be, in certain embodiments, potassium acetate, sodium acetate, zinc acetate, aluminum acetate, calcium acetate, magnesium acetate, magnesium oxide, copper acetate, lithium acetate, aluminum oxide, or zinc oxide.

In aspects where the method of the invention involves an acidic catalyst, the acidic catalyst, in certain embodiments, can be paratoluene sulfonic acid, dodecylbenzene sulfonic acid, borontrifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, or zinc chloride.

In certain other embodiments, the reacting step of the method of the invention can be conducted in the presence of a non-acidic solvent. According to some embodiments, the non-acidic solvent can be tetrahydrofuran, chloroform, dichloromethane, toluene, heptane, ethyl acetate, n-butyl acetate or hexane.

In still other embodiments, the reacting step of the method of the invention can be conducted in the absence of a solvent.

In certain embodiments of the invention, the reacting step is performed at about 60° C. to about 130° C. Depending on the source of formaldehyde used, the reaction step can be performed at about 20° C. to about 50° C., or about 30° C. to about 40° C. In still other instances, particularly, though not limited to, instances when the source of formaldehyde is a gas, the reaction step can be performed at about 0° C. to about 25° C.—provided the reaction mixture is a liquid at such temperatures.

In still further embodiments, the recovering step of the method of the invention can be by simple distillation, fractional distillation, flash distillation, steam distillation, vacuum distillation, short path distillation, thin-film distillation, reactive distillation, evaporation, extractive evaporation, flash evaporation, or rotary evaporation. In other embodiments, the recovering step can be repeated two or more times, or three or more times, or four or more times, or five or more times, or six or more times, or seven or more times, or eight or more times, or nine or more times or about ten times or more.

In certain other embodiments, the recovering step of the method of the invention can be performed at reduced pressure.

In still other embodiments, the malonic acid ester for use in the method of the invention can have the formula:

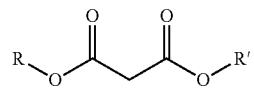

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl;

or wherein R and R' are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl.

In still other embodiments, the malonic acid ester can be monofunctional. In other embodiments, the malonic acid ester can be difunctional or even multifunctional.

In a further aspect, the present invention relates to a methylene malonate monomer prepared according to a method of the invention.

The methylene malonate monomers of the invention can be used to make products, including but not limited to, an adhesive, a coating, a sealant, a composite, or a surfactant. Such products, in various embodiments, can further comprise an acidic stabilizer, a free radical stabilizer, a sequestering agent, a cure accelerator, a rheology modifier, a plasticizing agent, a thixotropic agents, a natural rubber, a synthetic rubbers, a filler agent, a reinforcing agent or a combination thereof.

In certain embodiments, the acid stabilizer can have a pKa in the range of −15 to 5, or in the range of −15 to 3, or in the range of −15 to 1.

In some embodiments, the acid stabilizer is a volatile acid stabilizer with a boiling point less than 200° C.

In other embodiments, the acid stabilizer is a volatile acid stabilizer with a boiling point less than 170° C.

In still other embodiments, the acid stabilizer is a volatile acid stabilizer with a boiling point less than 130° C.

In other embodiments, the acid stabilizer can be an acidic gas, such as, for example, $SO_2$ or $BF_3$.

In some embodiments, the acid stabilizer can be present in a concentration of about 0.1 ppm to about 100 ppm, or from about 0.1 ppm to about 50 ppm, or from about 0.1 ppm to about 25 ppm, or from about 0.1 ppm to about 15 ppm.

In other embodiments, the methylene malonate products prepared according to the methods of the invention may also include a free radical stabilizer, such as a phenolic free radical stabilizer, and may be present in a concentration of about 0.1 ppm to about 10000 ppm, or from about 0.1 ppm to about 3000 ppm, or from about 0.1 ppm to about 1500 ppm, or from about 0.1 ppm to about 1000 ppm, or from about 0.1 ppm to about 300 ppm, or from about 0.1 ppm to about 150 ppm.

In still other embodiments, the methylene malonate products prepared according to the methods of the invention may also comprising a sequestering agent, wherein the sequestering agent can be a crown ether, a silyl crown, a calixarene, a polyethylene glycol, or a combination thereof.

In yet another embodiment, the methylene malonate products prepared according to the methods of the invention may also comprise a cure accelerator, wherein the cure accelerator is sodium acetate, potassium acetate, tetrabutyl ammonium fluoride, tetrabutyl ammonium chloride, tetrabutyl ammonium hydroxide, or combinations thereof.

In still another embodiment, the methylene malonate products prepared according to the methods of the invention may also comprise a rheology modifier, wherein the rheology modifier is hydroxyethylcellulose, ethyl hydroxyethylcellulose, methylcellulose, a polymeric thickener, pyrogenic silica or a combination thereof.

In yet another embodiment, the present invention relates to an adhesive product or composition comprising a methylene malonate monomer prepared according to a method of the invention and which is stable for at least one year.

In other embodiments, the adhesive products formed by a method of the invention, wherein the level of ketals is less than about 100 ppm, or less than about 50 ppm, or less than about 25 ppm, or less than about 10 ppm, or less than about 5 ppm, or even less than about 0.1 ppm, or less.

In still other embodiments, the adhesive products formed by a method of the invention, wherein the level of other latent acid-forming impurities is less than about 100 ppm, or less than about 50 ppm, or less than about 25 ppm, or less than about 10 ppm, or less than about 5 ppm, or even less than about 0.1 ppm, or less.

In yet another aspect, the present invention relates to a polymer comprising one or more units of a methylene malonate monomer prepared according to a method of the invention, and further relates to a product comprising said polymer.

The polymer product can be, but is not limited to, a sealant, a thermal barrier coating, a textile fiber, a water-treatment polymer, an ink carrier, a paint carrier, a packaging film, a molding, a medical polymer, a polymer film, a polymer fiber or a polymer sheet.

In yet another aspect, the present invention provides an enolate associated oligomer comprising one or more units of a methylene malonate monomer wherein the methylene malonate monomer is present as its enolic tautomer. The oligomer can be bound through hydrogen bonding of the enolic tautomer with water, formaldehyde, methylene glycol or a solvent capable of hydrogen bonding.

In still another aspect, the invention relates to a polymer having a repeat unit of the formula:

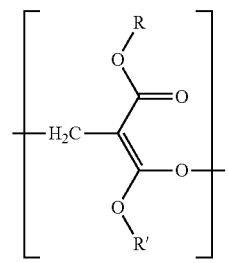

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl.

In still another embodiment, the invention provides a polymer having repeat units of the formula:

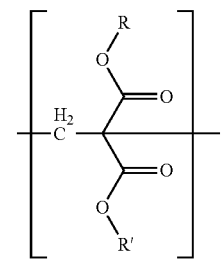

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl.

These and other embodiments are disclosed or are obvious from and encompassed by, the following Detailed Description.

BRIEF DESCRIPTION OF THE DRAWINGS

So that those having ordinary skill in the art to which the subject invention pertains will more readily understand how to make and use the invention as described herein, preferred embodiments thereof will be described in detail below, with reference to the drawings, wherein.

DESCRIPTION OF THE INVENTION

Overview

Figure 1:
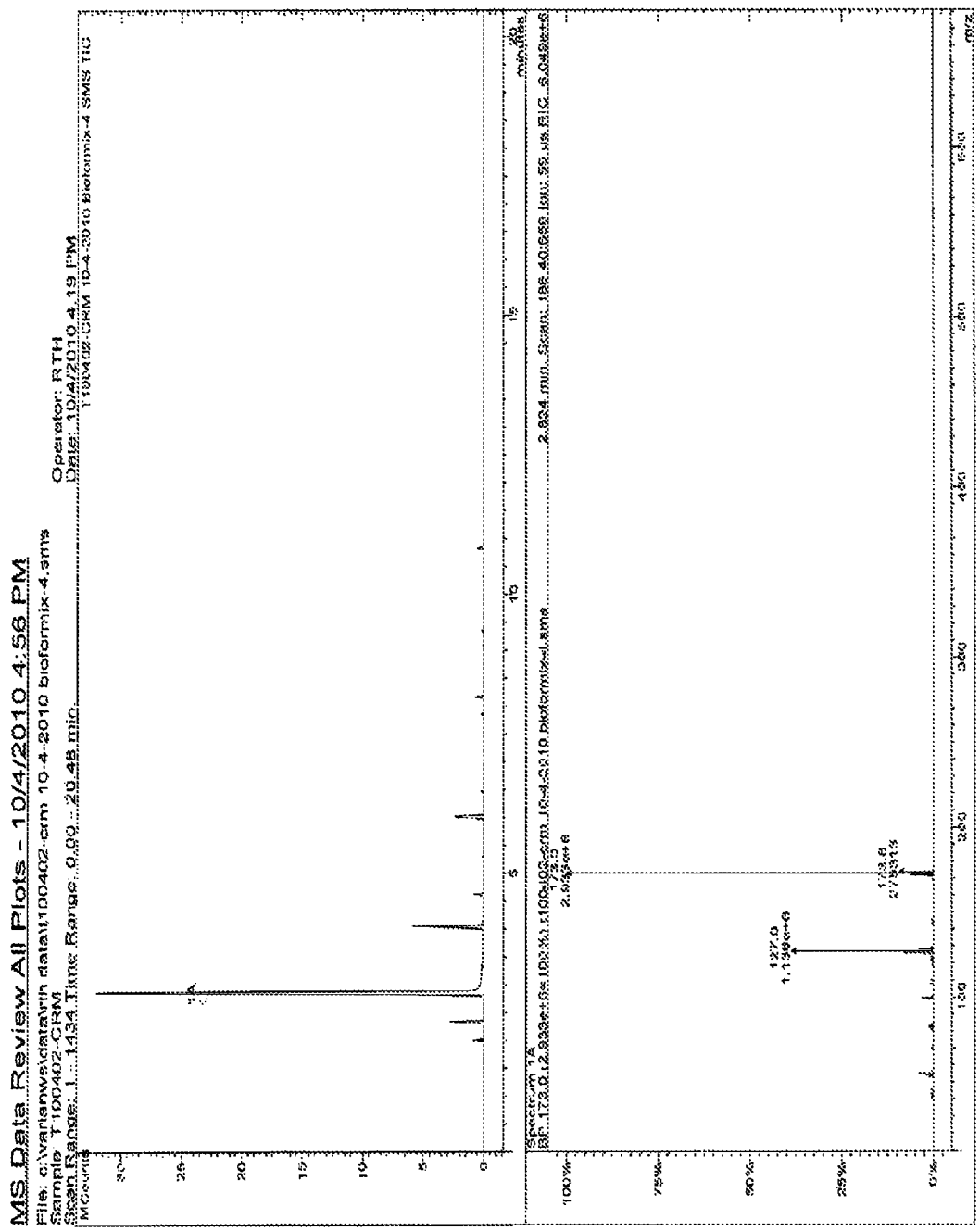
FIG. 1 depicts provides a GC-MS spectrum of crude diethyl methylene malonate monomer containing water, formaldehyde and other impurities.

The present invention provides new and nonobvious improvements in the use and application of the Knovenagel reaction in the synthesis of methylene malonate ("MM") monomers. The inventive method is advantageous over previously known approaches for synthesizing MM monomers, in part, because the methods of the invention, inter alia, (a) significantly reduce or eliminate the formation of alternative products, (b) significantly reduce or eliminate unwanted consumption of MM monomer products, and (c) significantly reduce or eliminate the degradation of MM monomer products. These advantages result in MM monomers, which upon recovery, are of higher quality, greater purity, improved yield and possess overall improved performance characteristics (e.g., improved cure speed, retention of cure speed, improved shelf-life and/or stability). Without intending to be bound by theory, the improved methods of the invention relate to the surprising discovery that the prior art entirely failed to recognize that alternative product formation, MM monomer consumption and MM degradation were widespread in prior synthesis methods and that these phenomena prevented the production of MM monomers that suitably could be used in the manufacture of MM-based products and materials.

The present invention overcomes these deficiencies in the prior art by varying the reaction conditions in unexpected ways not previously contemplated, the effects of which are to, inter alia: eliminate or significantly reduce the formation of deleterious side-products, i.e., provide a more highly purified reaction product; significantly reduce or eliminate unwanted consumption of methylene malonate monomer products via, e.g., formation of spurious oligomeric or polymeric compositions; significantly reduce or eliminate the degradation of methylene malonate monomer products; and improve the stability and reactivity of the methylene malonate monomer products, to allow for commercially and/or industrial-scale levels of the chemical synthesis and/or polymerization of products derived from or prepared from the methylene malonate monomers, e.g., adhesives, inks, coatings, paints, and the like.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "methylene malonate" refers to a compound having the core formula —O—C(O)—C(=CH$_2$)—C(O)—O—.

As used herein, the term "malonic acid ester" refers to a compound having the core formula —O—C(O)—CH$_2$—C(O)—O—. Equivalent terms known in the art may also be used.

As used herein, the term "malonic mono-acid mono-ester" refers to a compound having the core formula —O—C(O)—CH$_2$—C(O)—OH. Equivalent terms known in the art may also be used.

As used herein, the term "monofunctional" refers to a malonic acid ester or a methylene malonate having only one core formula.

As used herein, the term "difunctional" refers to a malonic acid ester or a methylene malonate having two core formulas bound through an alkylene linkage between one oxygen atom on each of two core formulas.

As used herein, the term "multifunctional" refers to refers to a malonic acid ester or a methylene malonate having more than one core formula which forms a chain through an alkylene linkage between one oxygen atom on each of two adjacent core formulas. In certain embodiments, the term multifunction refers to a malonic acid ester having 3, 4, 5, 6, 7, 8, 9, or 10 or more core formulas.

As used herein, the term "inactivating," as in inactivating the catalyst, refers to removing the catalyst or significantly reducing or eliminating the activity of the catalyst from the reaction mixture such that the catalyst no longer participates in the reaction. Such inactivation can be achieved by one of the methods described herein.

As used herein, the term "recovering" or "obtaining" as in recovering or obtaining the monomer, refers to the removal of the monomer from the reaction mixture by one of the methods described herein so it is in a substantially pure form.

As used herein, the term "latent acid-forming impurities" or "latent acid-forming impurity" refers to any impurity that, if present along with the recovered methylene malonate monomer, will with time be converted to an acid. The acid formed from these impurities tends to result in overstabilization of the methylene malonate monomer, thereby reducing the overall quality and reactivity of the monomer.

As used herein, the term "ketal" refers to molecule having a ketal functionality; i.e. a or molecule containing a carbon bonded to two —OR groups, where O is oxygen and R represents any alkyl group.

As used herein, the term "sterically hindered" refers to a compound in which the size of groups within the molecule prevents chemical reactions that are observed in related smaller molecules.

As used herein, the terms "volatile" and "non-volatile" refers to a compound which is capable of evaporating readily at normal temperatures and pressures, in the case of volatile; or which is not capable of evaporating readily at normal temperatures and pressures, in the case of non-volatile As used herein, the term "heat transfer agent" refers to a material which is capable of achieving a high temperature and transferring that temperature to a reaction mixture. Such heat transfer agents are typically able to reach temperatures from about 150° C. to about 300° C. and include, but are note limited to silica, silicone oil, mineral oil, a petroleum based heat transfer oil or a synthetic chemical based heat transfer oil.

As used herein, the term "enolate-associated oligomer" refers to an oligomer compound which is not formed by direct bonding of the monomers but is formed by a hydrogen bonded or other loosely associated bond between two monomers which are present as enol tautomers.

As used herein, the term "reaction mixture" refers to the combination or mixture of one or more reactants, solvents, catalysts or other materials in a reaction vessel which are capable of performing a chemical reaction. The use of the term "reaction mixture" does not indicate that a chemical reaction is occurring but merely conveys the combination or association of the materials within the reaction vessel. In certain embodiments, the term "reaction mixture" refers to the contents of the reaction vessel.

As used herein, the term "reaction complex" refers to the materials which result after reacting a malonic acid ester with a source of formaldehyde. Such reaction complexes may comprise, without limitation, methylene malonate monomers, oligomeric complexes, irreversible complex impurities, starting materials, or latent acid-forming impurities. In certain embodiments, the term "reaction complex" refers to the combination or mixture of one or more reactants, solvents, catalysts or other materials in a reaction vessel which are capable of performing a chemical reaction. The use of the term "reaction complex" does not indicate that a chemical reaction is occurring but merely conveys the combination or association of the materials within the reaction vessel. In certain embodiments, the term "reaction complex" refers to the contents of the reaction vessel. In certain embodiments, the term "reaction mixture" and "reaction complex" may be used interchangeably.

As used herein, the term "stabilized," e.g., in the context of "stabilized" methylene malonates or compositions comprising same, refers to the tendency of the methylene malonates (or their compositions) of the invention to substantially not polymerize with time, to substantially not harden, form a gel, thicken, or otherwise increase in viscosity with time, and/or to substantially show minimal loss in cure speed (i.e., cure speed is maintained) with time.

As used herein, the term "shelf-life," e.g., as in the context of methylene malonates having an improved "shelf-life," refers to the methyelene malonates of the invention which are stabilized for a given period of time, e.g., 1 month, 6 months, or even 1 year or more.

As used herein, the term "reaction vessel" refers to any container in which the reactants, solvents, catalysts or other materials may be combined for reaction. Such reaction vessels can be made of any material known to one of skill in the art such as metal, ceramic or glass.

Knovenagel Synthesis

The present invention contemplates an improved Knovenagel synthesis reaction for the synthesis of MM monomers, wherein the method, inter alia, (a) significantly reduces or eliminates the formation of alternative and/or deleterious side products, (b) significantly reduces or eliminates unwanted consumption of MM monomers and (c) significantly reduces or eliminates the degradation of MM monomers in the reaction and subsequent recovery and storage stages, i.e., improves stabilization of the monomers. These advantages are achieved based on the improvements discussed below.

The Knovenagel reaction with formaldehyde for the synthesis of methylene malonate monomers has been previously described. The typical Knovenagel reaction combines one mole of a malonic acid ester (e.g., a mono- or disubstituted malonate) and one mole of formaldehyde to form, via catalytic (chemical reaction) action in the presence of a basic catalyst and an acidic solvent, a methylene malonate monomer, as depicted in Schematic 1, below.

Schematic 1. Knovenagel reaction with formaldehyde for the synthesis of a methylene malonates.

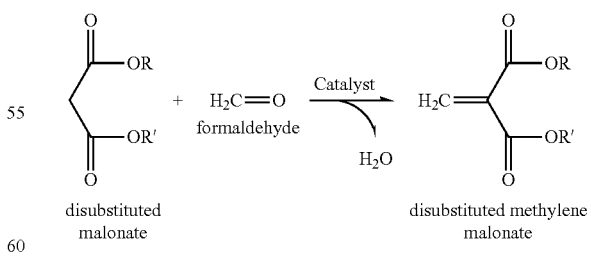

This reaction scheme is, however, fraught with difficulties. And, in most instances, the prior art did not even recognize its own problems. For instance, prior art use of the Knovenagel synthesis for preparing methylene malonates is typically carried out under conditions that leads to the formation of many different kinds of deleterious side products. In one example, the prior art teaches to conduct the Knovenagel reaction under acidic solvent conditions, for example, in acetic acid. The acetic acid or other weak organic acid then reacts with the formaldehyde to form a ketal, as depicted in the below schematic. The ketals co-distill with the methylene malonates and result in the contamination of the final preparation of the product. Over time, the ketals in the presence of water (spontaneously) hydrolyze and revert back to its acid form thereby increasing the acidic conditions of the product. The increased concentration of acid impinges on the ability of the monomer to polymerize, i.e., causing over stabilization of the monomer such that its overall reactivity and performance are significantly reduced.

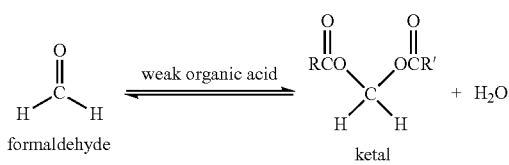

Besides ketal formation, the prior art was similarly unaware that its conditions for Knovenagel synthesis also led to the formation of other latent acid-forming species. These chemical species are formed as a result of various unintended side reactions that occur between reactants, or between reactants and solvent, or between reactants, solvents and products and even intermediate species that may form during the course of the reaction. These additional latent acid-forming species lead to the same result as the ketals, namely, that they are contaminants in the final methylene malonate product and with time they are converted back to an acid. With increasing acidic conditions, like with ketals, comes an overall reduction in the reactivity and performance of the monomer products.

An example of another impediment to forming high quality monomer through the Knovenagel reaction is the unwanted polymerization of the monomer. These polymerizations can be occur via polymerization of the monomers themselves, or of the monomers and various intermediates, or of the monomer and other side products that may be present in the reaction mixture under conditions used in the prior art. These polymerizations not only lead to unwanted consumption of the monomer product, but also may lead to the formation of other side products that may or may not become co-distilled with the methylene monomers themselves, causing the monomer product to become contaminated with unwanted side products that may impinge on the overall performance of the monomers.

Other deleterious events are also possible during the Knovenagel reaction, in particular, those events that result in the consumption of monomer or raw starting materials and the reduction in the yield of the desired methylene malonate product. For example, the methylene group can react with 2 formaldehyde molecules to form a dimethyl-ol material, which consumes raw material and is nonreactive. The malonate raw material can also react with a methylene malonate already formed, instead of formaldehyde, to produce a glutarate, which is also non-reactive and consumes raw material. In addition, the desired products formed can polymerize thereby reducing the yield of desired product.

Figure 2:
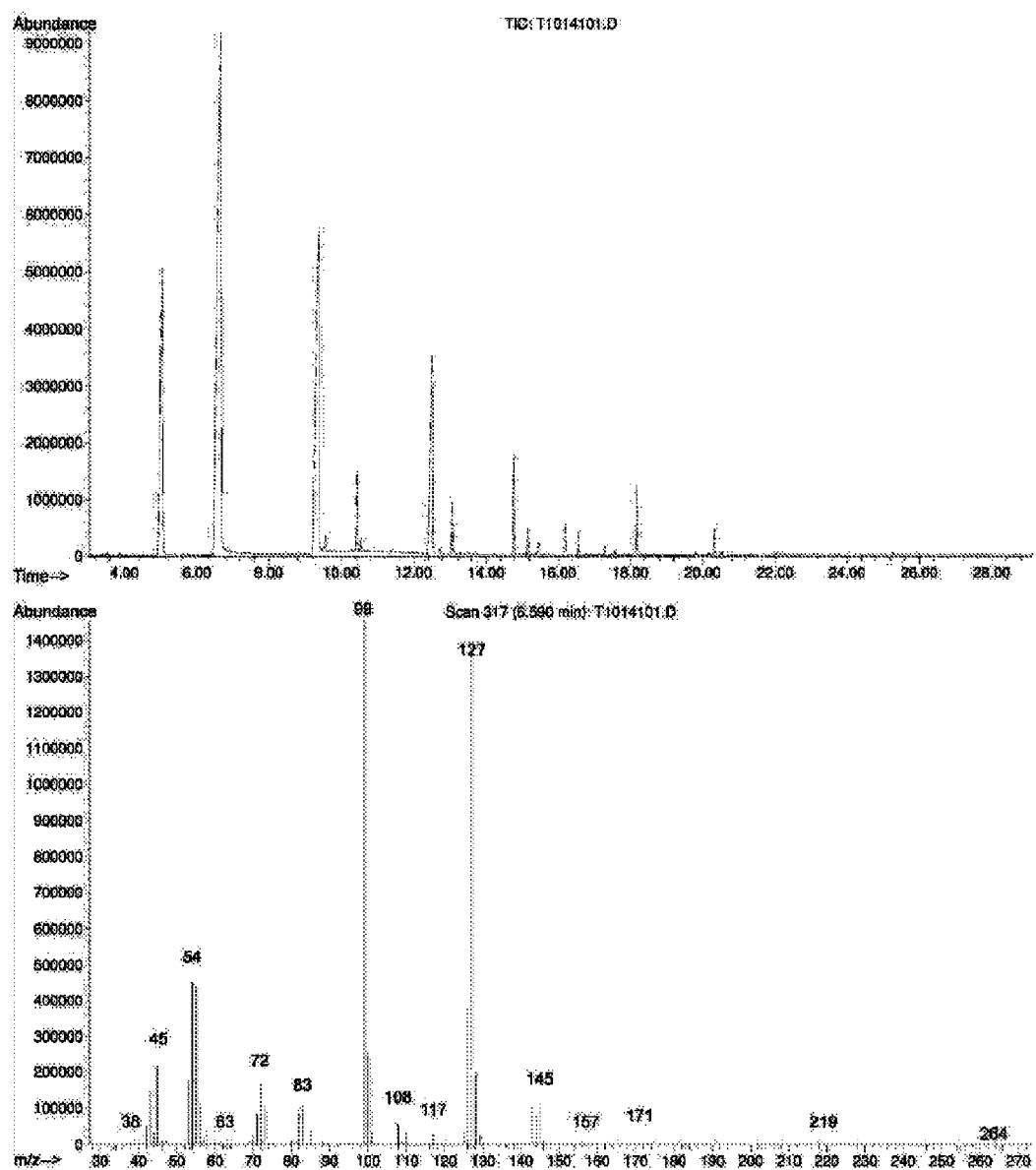
FIG. 2 depicts the depletion of the diethyl methylene malonate monomer of FIG. 1 over the course of storage at room temperature for 7 days, as depicted by GC-MS.
Figure 3:
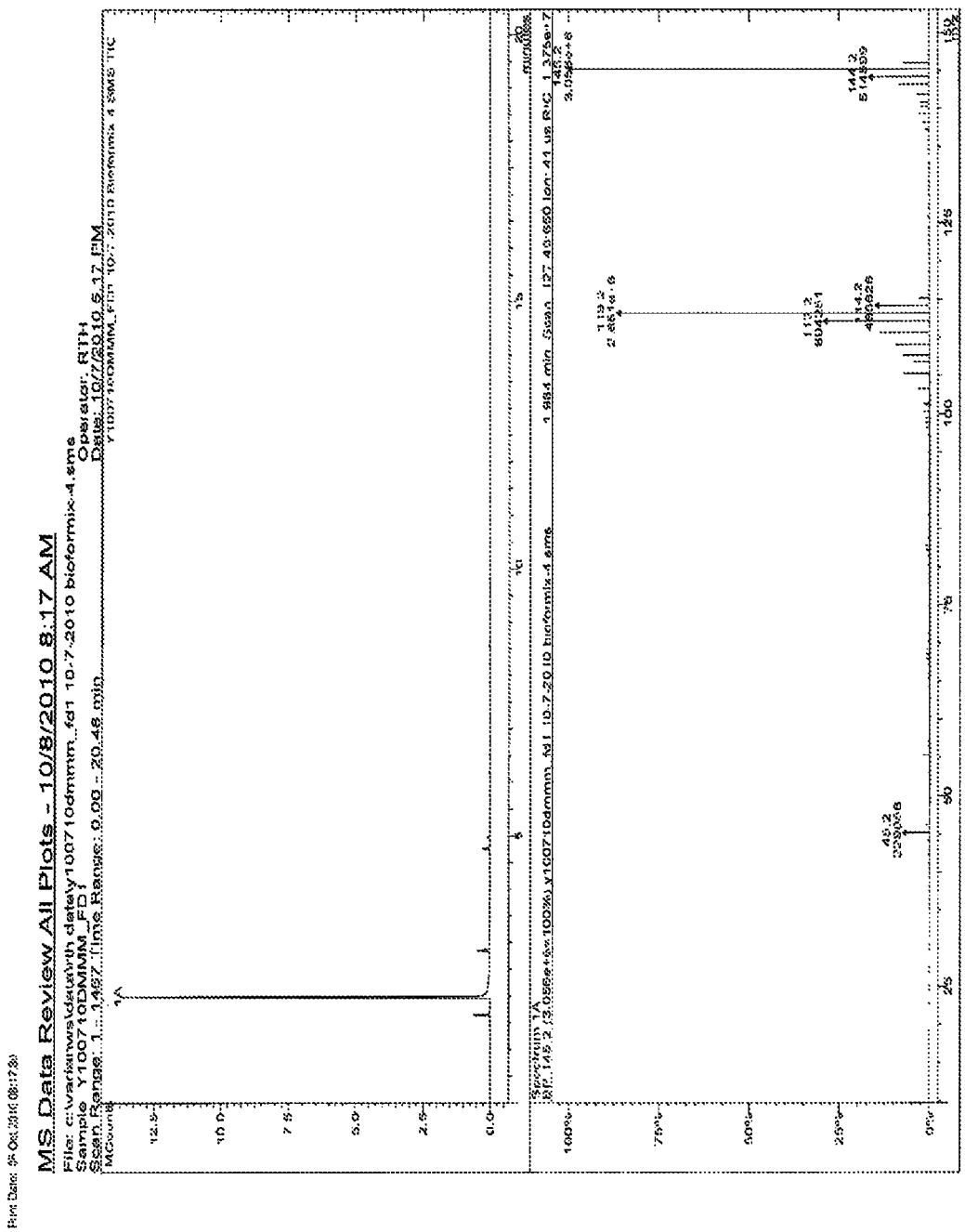
FIG. 3 depicts provides a GC-MS spectrum of crude dimethyl methylene malonate monomer containing water, formaldehyde and other impurities.
Figure 4:
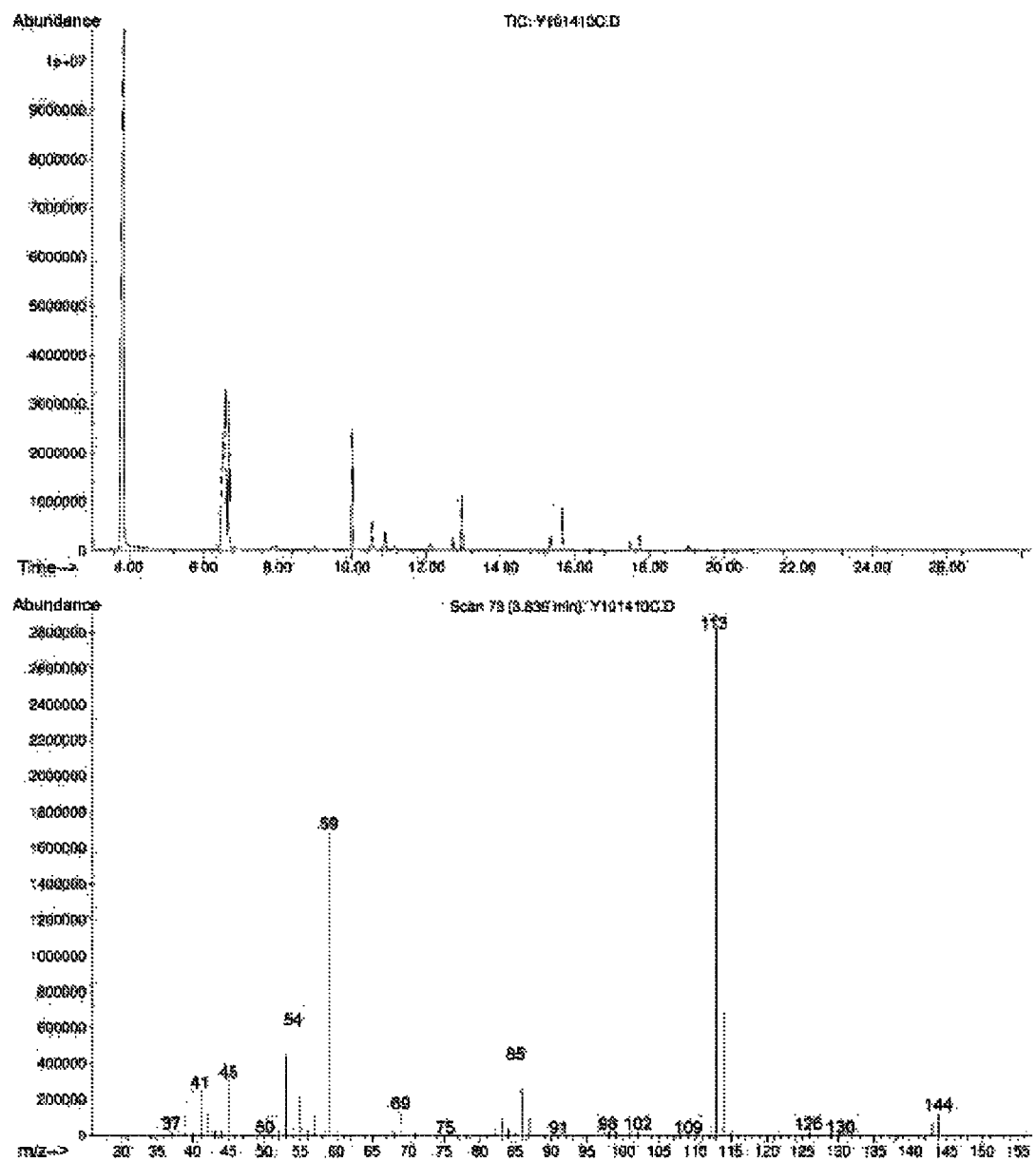
FIG. 4 depicts the depletion of the dimethyl methylene malonate monomer of FIG. 3 over the course of storage at room temperature for 7 days, as depicted by GC-MS.
Figure 5:
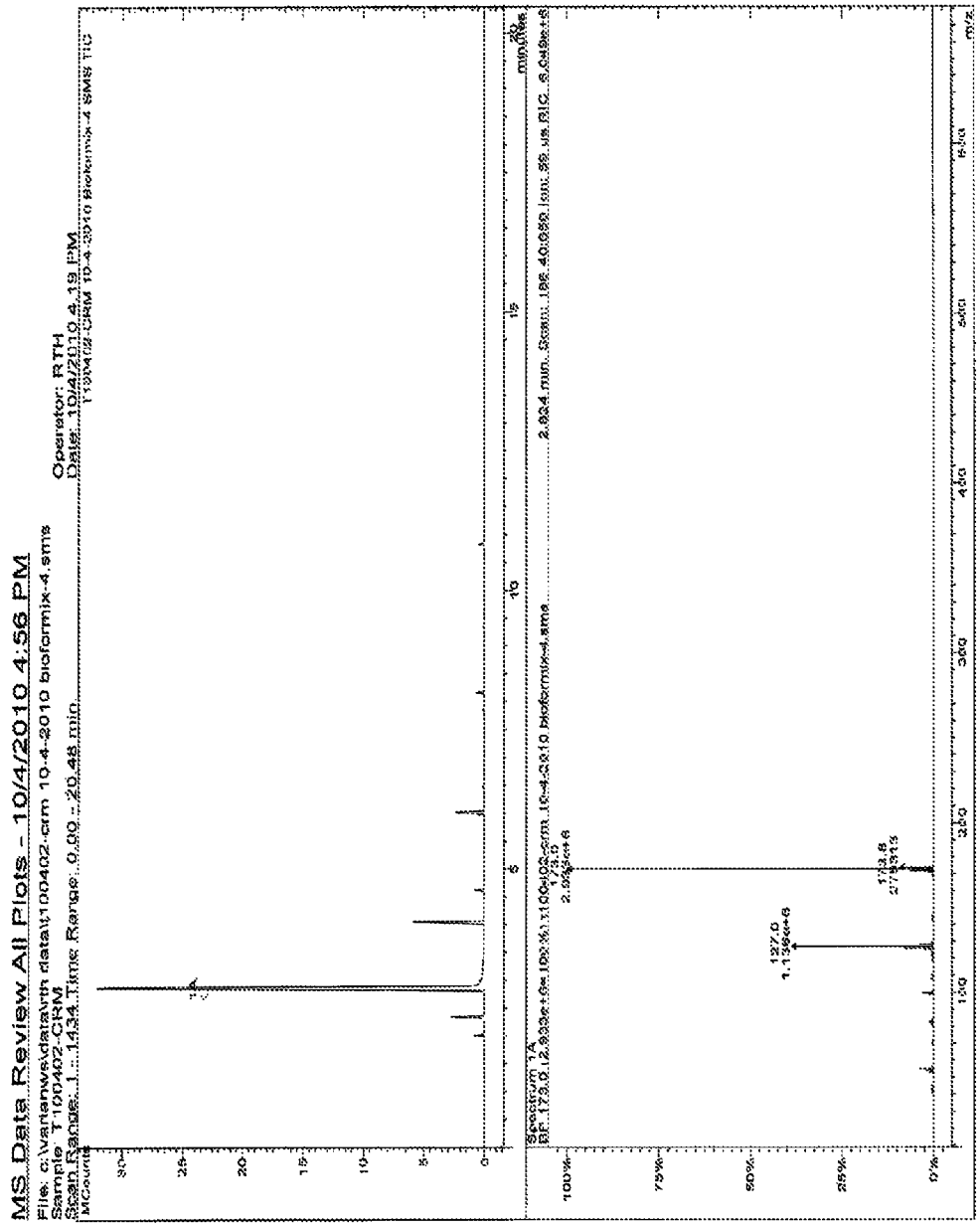
FIG. 5 depicts provides a GC-MS spectrum of crude diethyl methylene malonate monomer containing water, formaldehyde and other impurities.
Figure 6:
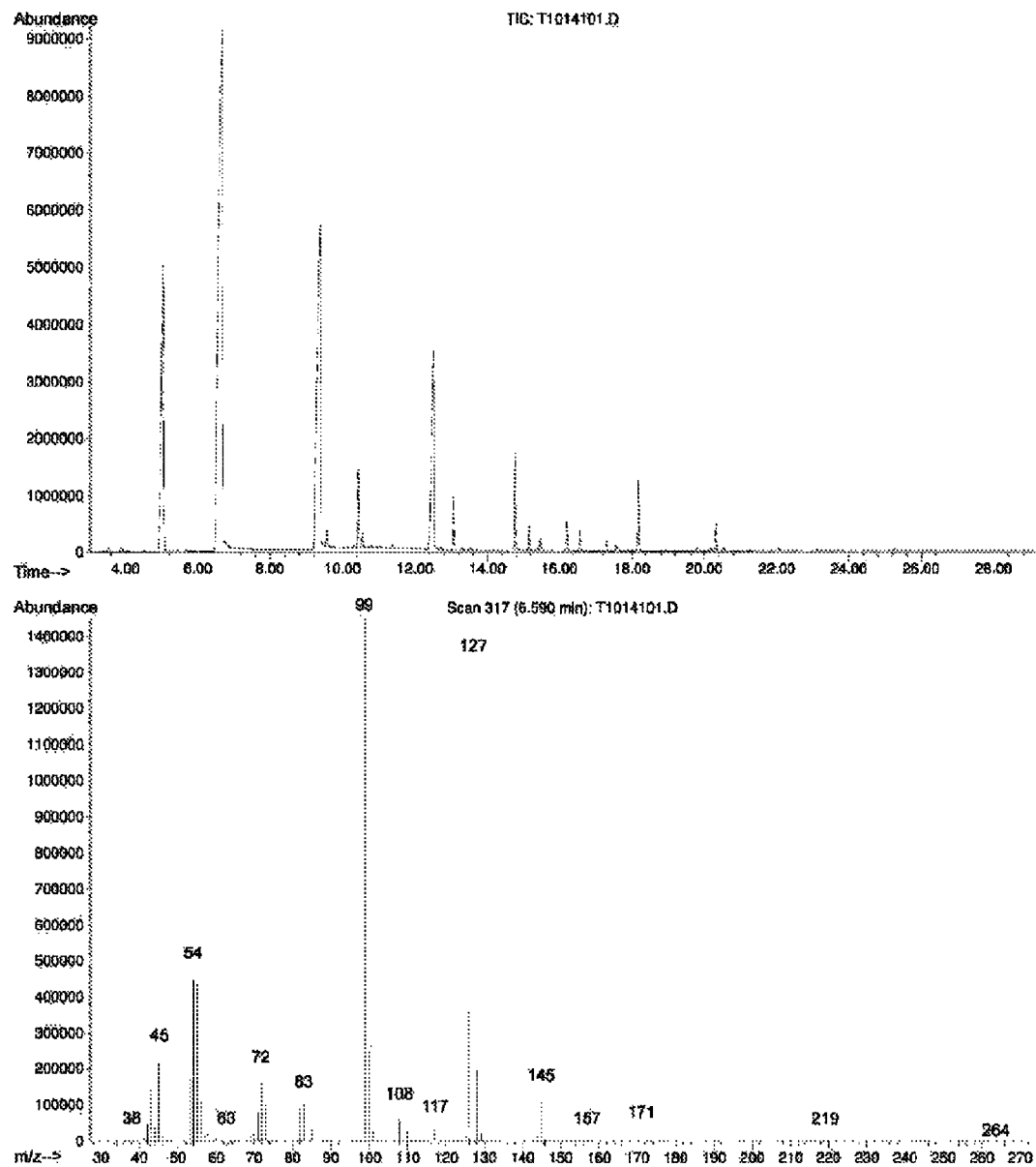
FIG. 6 depicts the depletion of the diethyl methylene malonate monomer of FIG. 5 over the course of storage at room temperature for 7 days, as depicted by GC-MS.
Figure 7:
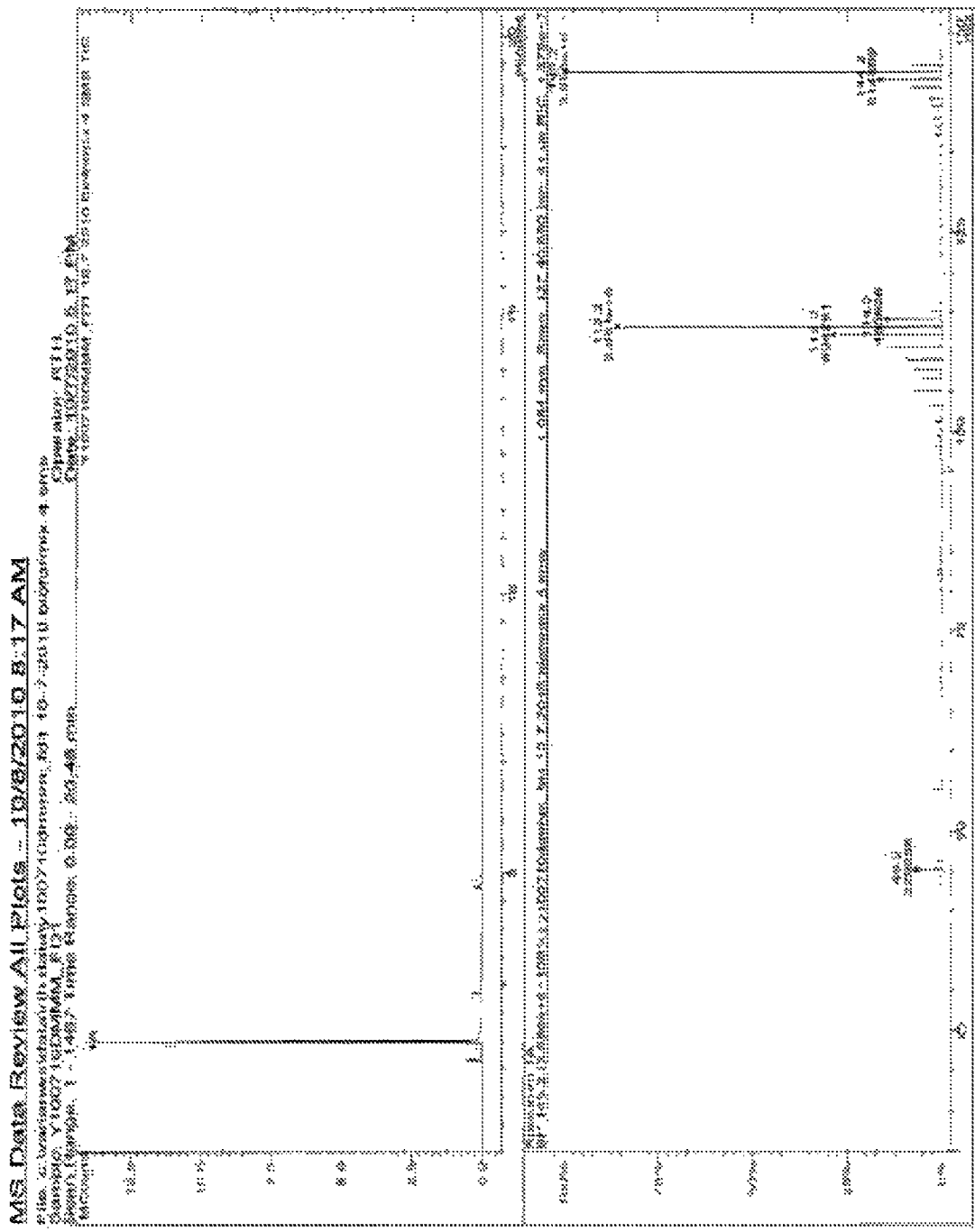
FIG. 7 depicts provides a GC-MS spectrum of crude dimethyl methylene malonate monomer containing water, formaldehyde and other impurities.
Figure 8:
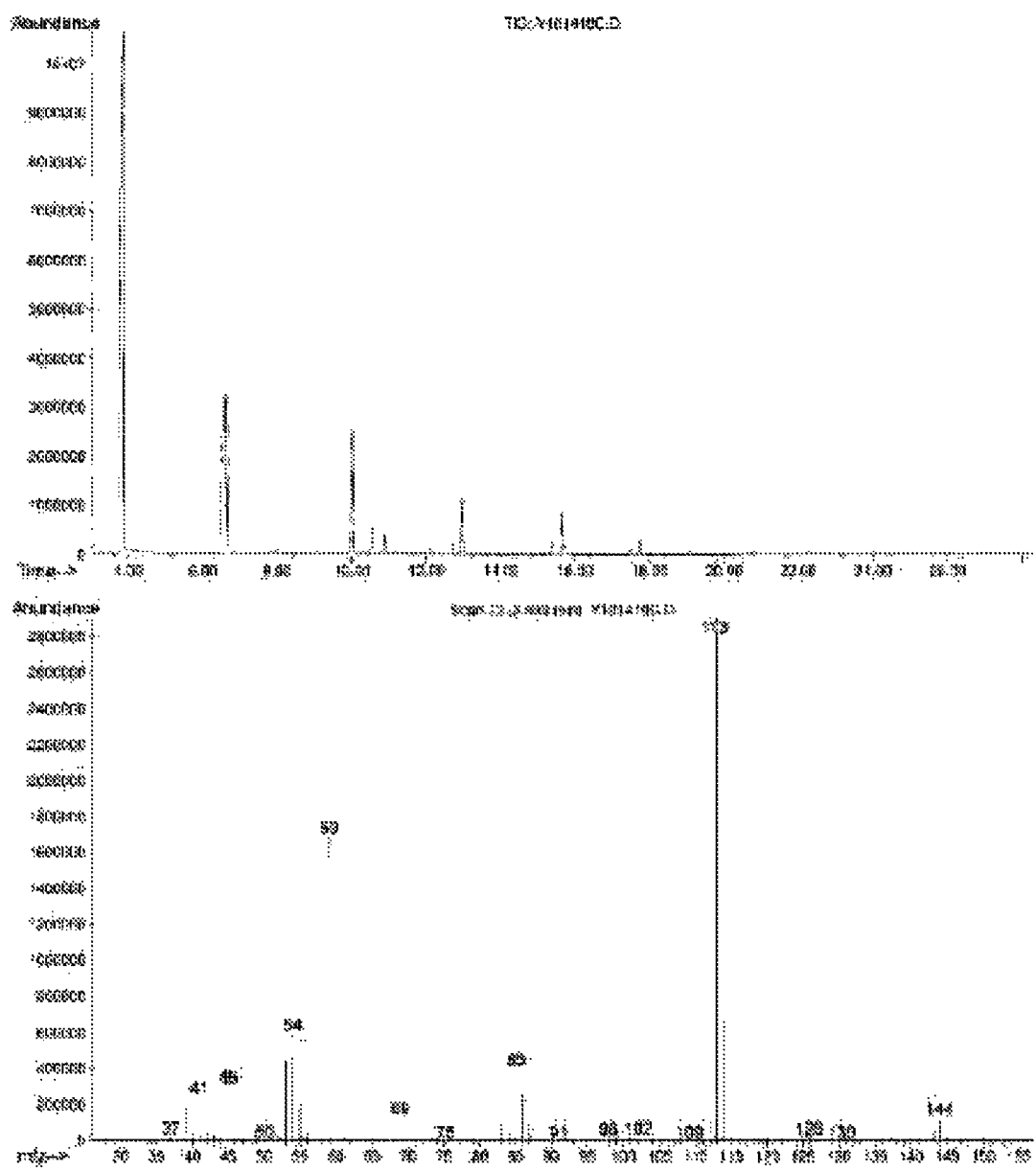
FIG. 8 depicts the depletion of the dimethyl methylene malonate monomer of FIG. 7 over the course of storage at room temperature for 7 days, as depicted by GC-MS.
Figure 9:
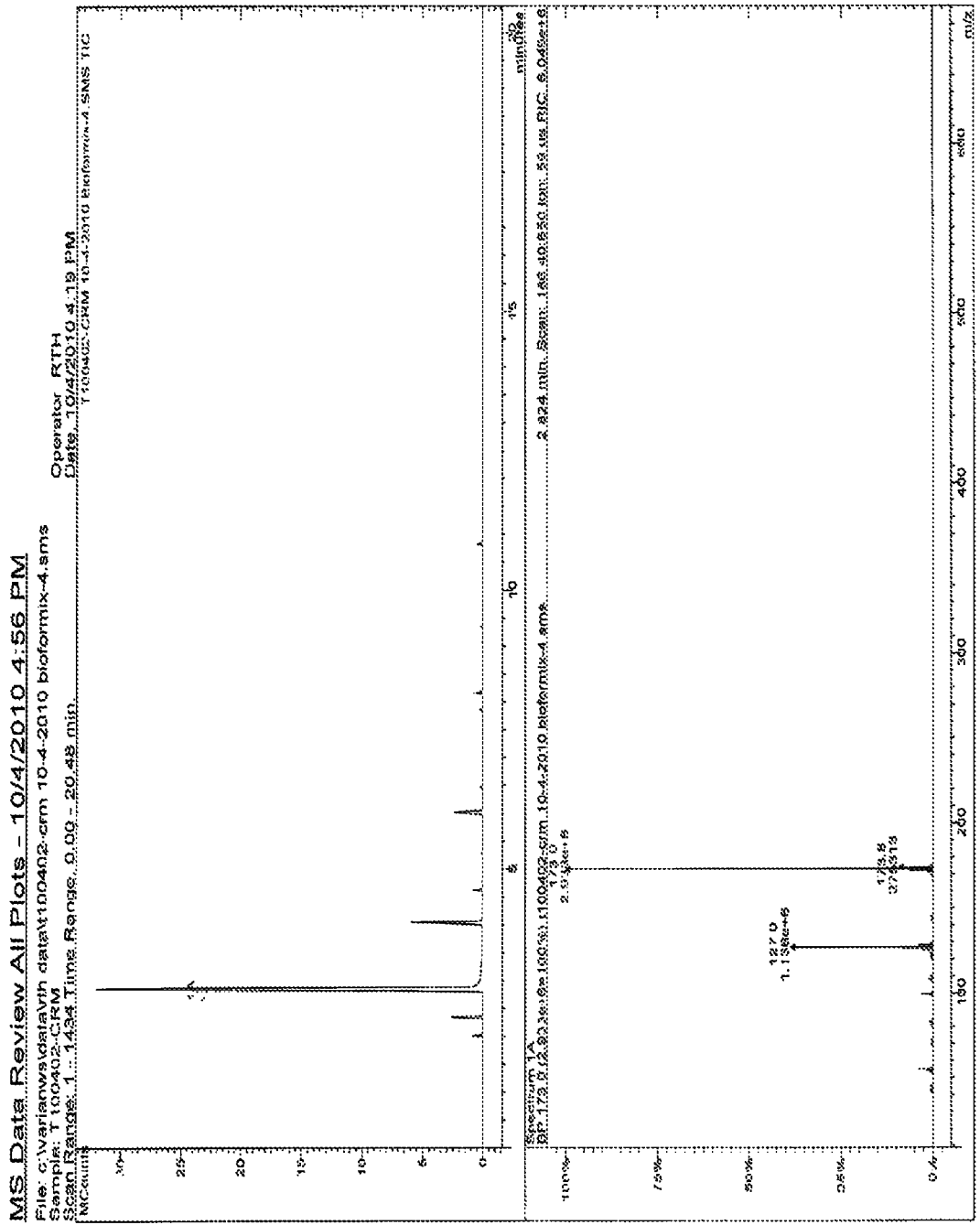
FIG. 9 depicts provides a GC-MS spectrum of crude diethyl methylene malonate monomer containing water, formaldehyde and other impurities.
Figure 10:
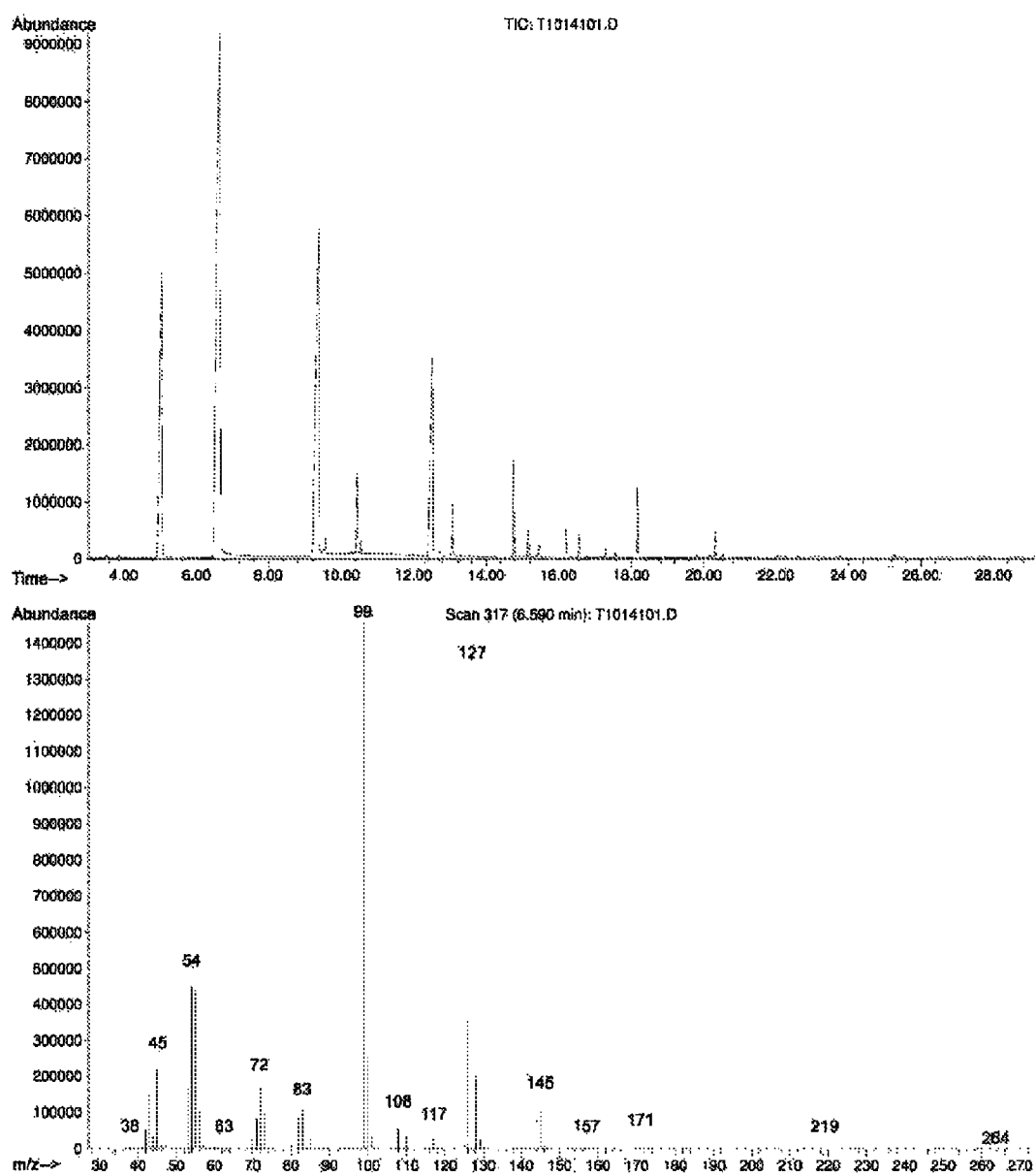
FIG. 10 depicts the depletion of the diethyl methylene malonate monomer of FIG. 9 over the course of storage at room temperature for 7 days, as depicted by GC-MS.

Exemplary evidence of deleterious side-reaction formation occurring during the Knovenagel reaction with formaldehyde has been observed by the present inventors, it is believed for the first time. The observed phenomenon is that methylene malonate monomers already formed by the Knovenagel reaction with formaldehyde, if left to stand at room temperature for a period of time, form a mixture that varies in composition to include various side products. In several observed cases, crude products still containing some amount of formaldehyde and water after 7 days, were reduced in yield by up to 40% due to the consumption of the already formed methylene malonate monomers in deleterious side reactions with other components of the reaction mixture. See, for example, FIGS. 1, 2, 3 and 4. The methylene malonates prepared under such conditions are unsuitable for use in making commercial products, including reactive formulated products, such as reactive adhesives, and polymer products, such as films, fibers, molded articles and the like.

Importantly, while a substantial amount of prior art exists on the use of the Knovenagel reaction for the preparation of methylene malonates (e.g., see U.S. Pat. Nos. 2,313,501; 2,330,033; 3,221,745; 3,523,097; 3,557,185; 3,758,550; 3,975,422; 4,049,698; 4,056,543; 4,160,864; 4,931,584; 5,142,098; 5,550,172; 6,106,807; 6,211,273; 6,245,933; 6,420,468; 6,440,461; 6,512,023; 6,610,078; 6,699,928; 6,750,298; and 2004/0076601, each of which are incorporated by reference), and the Knovenagel reaction for the synthesis of methylene malonates has been known at least since 1938 (see e.g., U.S. Pat. No. 2,313,501), the prior art did not recognize the above significant limitations. This is further evidenced by the fact that no single commercial product based on methylene malonates has ever been marketed or sold, including where the methylene malonates have been made using the Knovenagel reaction.

Improved Knovenagel Synthesis of the Invention

The present invention relates to an improved Knovenagel synthesis reaction involving the condensation of malonic acid esters with formaldehyde to form methylene malonate monomers, wherein the improvement is conducted in a variety of ways. The achieved objective of each of the approaches is the same, namely to (a) significantly reduce or eliminate the formation of alternative and/or deleterious side products, (b) significantly reduce or eliminate consumption of MM monomers (e.g., unwanted polymerization) and (c) significantly reduce or eliminate degradation of MM monomers in the reaction and during subsequent recovery and storage stages, i.e., maintain stability and reactivity of MM monomers.

According to one aspect of the invention, the method of the invention is carried out with the step of inactivating the catalyst. The present inventors surprisingly discovered that catalyst inactivation provides for, inter alia, (a) significantly reduced or eliminated formation of alternative products, (b) significantly reduced or eliminated consumption of MM monomers and (c) significantly reduced or eliminated degradation of MM monomers in the reaction and during subsequent recovery and storage stages. To the inventors' knowledge, catalyst inactivation has not previously been recognized or contemplated in the context of using the Knovenagel reaction with formaldehyde to synthesize methylene malonates.

Accordingly, the present invention relates, in part, to the complete or substantial inactivation of the reaction catalyst to eliminate or significantly reduce the reactivity or subsequent further reaction of the mixture, which can lead to methylene malonate consumption, degradation or the formation of alternate products, all of which can impede yield optimization, methylene malonate purification and methylene malonate polymerization and other aspects of product performance and manufacture. The prior art that employs the Knovenagel reaction to synthesize methylene malonates does not in any way teach, suggest or exemplify this additional step. By contrast, the prior art methods for synthesizing methylene malonates are associated with a variety of problems which preclude their use in making viable MM-based products. Such problems include, for example, large-scale losses in monomer yield due to monomer degradation during the reaction and subsequent recovery stages, generation of unwanted, deleterious alternate products during the reaction and downstream processes, and the production of metal and acid/base residues from the catalyst, which become concentrated during recovery. These problems can significantly impinge on the overall quality of the monomers, their reactivity, stability and capacity for forming viable commercial products. For example, in the case of adhesives, these kinds of problems lead to a significant reduction in the cure speed and an overall reduction in shelf-life of the product.

According to another aspect of the invention, the method of the invention is carried out with the step of reacting the malonic acid ester with a source of formaldehyde in the presence of an acidic catalyst. Generally the prior art conducted the Knovenagel reaction using a basic catalyst; however, since the basic catalysts promotes the polymerization of the MM monomers once they are formed, the acid catalyst avoids or at least substantially reduces the occurrence of unwanted polymerization of the MM monomers after they are formed, thereby significantly reducing or eliminating the unwanted consumption of MM monomers in the reaction mixture.

According to yet another aspect of the invention, the method of the invention is carried out with the further step of minimizing the recovery of volatile latent acid forming impurities from the reaction complex, such as ketals, which can co-distill with the MM monomer products and then revert to their acidic form with time. Once in their acidic form, the acidic environment increases, which further blocks or weakens the reactivity of the MM monomers as they are stabilized against polymerization. This can be particularly relevant to the use of MM monomers in the context of adhesives, where the increased acid content with time due to the presence of such volatile latent acid forming impurities can impinge on the overall reactivity and cure speed, etc., of the monomer products.

While the invention generally relates to an improved Knovenagel reaction with formaldehyde to synthesize methylene malonate monomers, the present invention should not be limited as such. The present inventors have generally recognized it is believed for the first time general concept that the performance and overall quality of MM monomers is particularly sensitive to the presence of unwanted alternative and deleterious side products and unwanted monomer degradation and/or consumption is widely applicable to any type of synthesis that can be used to generate methylene malonates. Prior to the present invention, the significance and nature of these types of impurities and their effects on the performance and quality of methylene malonates was not previously contemplated. Thus, for the first time, the present invention provides a viable approach to producing methylene malonate monomers that can be utilized as the basis for viable consumer and industrial monomer-based (e.g., adhesives) and polymer-based (e.g., fibers) products.

In certain embodiments of the invention, the reacting step is performed at about 60° C. to about 130° C. Depending on the source of formaldehyde used, the reaction step can be performed at about 20° C. to about 50° C., or about 30° C. to about 40° C. In still other instances, particularly, though not limited to, instances when the source of formaldehyde is a gas, the reaction step can be performed at about 0° C. to about 25° C.—provided the reaction mixture is a liquid at such temperatures.

These particular aspects of the invention are not meant to be limiting, and other embodiments and aspects of the invention exist as indicated below.

Reactants

The Knovenagel reaction for making methylene malonates of the invention includes at least two basic reactants: a malonic acid ester and a source of formaldehyde.

In certain embodiments, the present invention contemplates the use of malonic acid esters having the following formula:

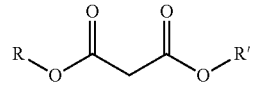

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl;

or wherein R and R' are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl.

In certain other embodiments, the present invention contemplates the following specifically identified malonic acid esters: dimethyl, diethyl, ethylmethyl, dipropyl, dibutyl, diphenyl, and ethyl-ethylgluconate, among others.

In certain other embodiments, the present invention contemplates the use of malonic acid esters having the following formula:

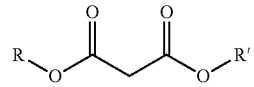

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl.

The malonic acid esters may be derived or obtained from any source, including any commercial source, derived from nature, other compounds, synthesized by other processes, etc. In certain embodiments, the malonic acid esters are obtained from "green" sources. For example, the malonic acid esters can be derived from biological sources, such as via fermentation production systems whereby microorganisms generate the malonic acid esters as direct metabolic by-products of fermentation—or whereby the microorganisms generate metabolic by-products of fermentation that can be then converted inexpensively to the desired malonic acid esters. These fermentation production systems are well-known in the art and may utilize either—or both—microorganisms derived from nature or engineered microorganisms that are specifically designed to produce the desired malonic acid ester products, e.g., recombinant or engineered *Escherichia coli*.

In another embodiment of the invention, the malonic acid ester reactant is mono functional.

In still another embodiment of the invention, the malonic acid ester reactant is difunctional.

In still another embodiment of the invention, the malonic acid ester reactant is multifunctional.

In certain embodiments, the present invention contemplates the use of malonic mono-acid mono-esters having the following formula:

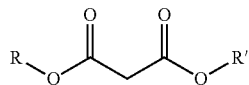

wherein one of R and R' is hydrogen and the other is are $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy —(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl —($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, ester or sulfonyl.

In another embodiment of the invention, the malonic mono-acid mono-ester reactant is monofunctional.

In still another embodiment of the invention, the malonic mono-acid mono-ester reactant is difunctional.

In still another embodiment of the invention, the malonic mono-acid mono-ester reactant is multifunctional.

The malonic mono-acid mono-esters may be derived or obtained from any source, including any commercial source, derived from nature, other compounds, synthesized by other processes, etc. In certain embodiments, the malonic mono-acid mono-esters are obtained from "green" sources. For example, the malonic mono-acid mono-esters can be derived from biological sources, such as via fermentation production systems whereby microorganisms generate the malonic mono-acid mono-esters as direct metabolic by-products of fermentation—or whereby the microorganisms generate metabolic by-products of fermentation that can be then converted inexpensively to the desired malonic mono-acid mono-esters. These fermentation production systems are well-known in the art and may utilize either—or both—microorganisms derived from nature or engineered microorganisms that are specifically designed to produce the desired malonic mono-acid mono-esters products, e.g., recombinant or engineered *Escherichia coli*.

In certain other embodiments, the present invention contemplates the use of malonic di-acids having the following formula:

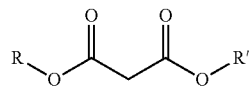

wherein R and R' are both hydrogen.

The malonic di-acids may be derived or obtained from any source, including any commercial source, derived from nature, other compounds, synthesized by other processes, etc. In certain embodiments, the malonic di-acids are obtained from "green" sources. For example, the malonic di-acids can be derived from biological sources, such as via fermentation production systems whereby microorganisms generate the malonic di-acids as direct metabolic by-products of fermentation—or whereby the microorganisms generate metabolic by-products of fermentation that can be then converted inexpensively to the desired malonic di-acids. These fermentation production systems are well-known in the art and may utilize either—or both—microorganisms derived from nature or engineered microorganisms that are specifically designed to produce the desired malonic di-acids products, e.g., recombinant or engineered *Escherichia coli*.

Further reference to the methods, materials and procedures for preparing and/or obtaining mono functional, difunctional and multifunctional malonic acids, malonic di-acids, or malonic mono-acid mono-esters can be found in U.S. Pat. Nos. 7,663,000 (Quinoneimines of malonic acid diamides); 7,553,989 (Malonic acid monoesters and process for producing the same); 7,208,621 (Malonic acid monomethyl derivatives and production process thereof); 7,109,369 (Malonic acid monomethyl derivatives and production process thereof); 6,794,365 (Malonic acid derivatives, processes for their preparation their use and pharmaceutical compositions containing them); 6,673,957 (Method for producing alkoxy malonic acid dinitriles); 6,613,934 (Enantiomerically enriched malonic acid monoesters substituted by a tertiary hydrocarbon radical, and their preparation); 6,559,264 (Malonic acid ester/triazole mixed blocked HDI trimer/formaldehyde stabilization); 6,395,931 (Malonic acid and esters thereof); 6,395,737 (Malonic acid derivatives, processes for their preparation, for their use and pharmaceutical compositions containing them); 6,284,915 (Process for preparing 2-amino malonic acid derivatives and 2-amino-1,3-propanediol derivatives, and intermediates for preparing the same); 6,238,896 (Process for producing malonic acid derivatives); 5,886,219 (Process for preparing malonic acid and alkylmalonic acids); 5,817,870 (Process for the production of malonic acid or a salt thereof); 5,817,742 (Polymer-conjugated malonic acid derivatives and their use as medicaments and diagnostic agents); 5,693,621 (Malonic acid derivatives having antiadhesive properties); 5,426,203 (Platinum complexes of malonic acid derivatives and process for the preparation thereof); 5,334,747 (Method of preparing substituted malonic ester anilides and malonic acid mono-anilides); 5,292,937 (Use of malonic acid derivative compounds for retarding plant growth); 5,210,222 (Process for the production of malonic acid anhydride); 5,162,545 (Malonic acid dyes and polycondensation products thereof); 5,039,720 (Aqueous electrophoretic enamel coating materials, which can be deposited at the cathode crosslinked with methane tricarboxylic acid amides of malonic acid derivatives); 5,021,486 (Hindered amine-substituted malonic acid derivatives of s-triazine); 4,914,226 (Malonic acid derivatives and methods for their synthesis); 4,835,153 (Malonic acid derivatives); 4,736,056 (Process for the production of malonic acid derivative compounds); 4,698,333 (Use of substituted malonic acid derivatives as agents for combating pests); 4,578,503 (Alkylated or alkenylated malonic acid or its derivatives having a fluorine); 4,556,649 (Substituted malonic acid diamide insecticides, compositions and use); 4,539,423 (Process for preparing diesters of malonic acid); 4,517,105 (Metalworking lubricant composition containing a novel substituted malonic acid diester); 4,504,658 (Epimerization of malonic acid esters); 4,444,928 (Polymeric malonic acid derivatives); 4,443,624 (Method of preparing malonic acid dialkyl esters); 4,399,300 (Method of preparing malonic acid dialkyl esters); 4,329,479 (Process for producing 1,3-dithiol-2-ylidene malonic acid dialkyl esters); 4,256,908 (Process for preparing diesters of malonic acid); 4,237,297 (Piperidine containing malonic acid derivatives); 4,198,334 (Substituted malonic acid derivatives and their use as stabilizers); 4,154,914 (Process for producing acrylic rubber by copolymerizing acrylic ester and malonic acid derivative having active methylene group); 4,105,688 (Process for the production of malonic acid dinitrile and purification thereof); 4,102,809 (Malonic acid composition for thermoparticulating coating); 4,079,058 (Process of performing cyclization reactions using benzyl or pyridylamino malonic acid derivatives); 4,046,943 (Malonic acid derivative composition for forming thermoparticulating coating); 4,036,985 (Mono substituted malonic acid diamides and process of preparing them); 3,995,489 (Malonic acid derivative composition for forming thermoparticulating coating); 3,936,486 (Process for the production of malonic acid dinitrile), each of which are incorporated by reference in their entireties by reference herein.

The methods of the invention also contemplate any suitable source of formaldehyde. For example, the formaldehyde may be synthesized, derived from another chemical species (e.g., paraformaldehyde), or obtained from nature or from some other suitable source. In certain embodiments, the formaldehyde is introduced in the form of a gas. In certain embodiments, the formaldehyde is obtained from paraformaldehyde. Commercial sources of formaldehyde and paraformaldehyde are readily available, which may include, for example, trioxane and formalin (e.g., aqueous formaldehyde).

Catalysts

The present invention contemplates the use of any suitable acidic or basic catalyst.

In certain embodiments, catalysts that are typically used for Knovenagel reactions with formaldehyde to make MM monomers are contemplated. Such catalysts include, for example, basic catalyst salts, such as, potassium acetate and the neutral co-catalyst copper acetate.

In certain other embodiments, the present invention contemplates catalysts that heretofor were previously unused in the context of the Knovenagel reaction with formaldehyde to synthesize MM monomers. Such catalysts include various acidic, basic, neutral, or even amphoteric catalysts.

Acidic catalysts can include, for example, lithium chloride, boron trifluoride etherate, ferric sulfate, zirconium oxychloride, cupric chloride, titanium tetrachloride, zinc chloride, aluminum oxide, or zinc oxide. Accordingly, the acidic catalysts of the invention may include, but are not limited to, paratoluene sulfonic acid, dodecylbenzene sulfonic acid, borontrifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, and zinc chloride.

Neutral catalysts can also include silica and other insoluble surface active agents.

In certain other embodiments, the inventive methods utilize a basic catalyst. Basic catalysts of the invention may include, but are not limited to, potassium acetate, sodium acetate, zinc acetate, zinc acetate dihydrate, aluminum acetate, calcium acetate, magnesium acetate, magnesium oxide, copper acetate, lithium acetate, aluminum oxide, and zinc oxide.

In still further embodiments, the amphoteric catalysts can include, but are not limited to, aluminum oxide, aluminum acetate, zinc acetate, magnesium acetate, and zinc oxide.

Catalyst Inactivation

In the context of the Knovenagel reaction with formaldehyde, the advantages of the inventive method, including, (a) significantly reduced or eliminated formation of alternative products, (b) significantly reduced or eliminated consumption of MM monomers and (c) significantly reduced or eliminated degradation of MM monomers in the reaction and during subsequent recovery and storage stages, are achieved, in part, by the inactivation of the catalyst used in the reaction.

Where a catalyst is utilized in the improved Knovenagel reaction of the invention, the present invention can include the step of catalyst inactivation.

Any suitable method or approach for inactivating the catalyst is contemplated by the present invention. In certain embodiments, it is preferred that the method for inactivating the catalyst fully eliminates the activity of the catalyst, i.e., 100% elimination of catalytic activity. In other embodiments, it is preferred that the activity of the catalyst is reduced by at least 50%, or at least by 55%, or at least by 60%, or at least by 65%, or at least by 70%, or at least by 75%, or at least by 80%, or at least by 85%, or at least by 90%, or at least by 95%, or at least by 99% relative to the activity of the catalyst absent the conditions that cause the inactivation, i.e., relative to 100% catalytic activity.

In one embodiment, catalyst inactivation can be achieved by the addition of an agent that leads to formation of an insoluble precipitate that can be filtered or otherwise physically separated from the reaction mixture or methylene malonates. The agent can be, for example, an acid that is added in an equimolar amount or in some excess (e.g., about 2×, or 3×, or 4× equimolar) to the molar amount of catalyst used. Additional solvents or other ingredients may be added to facilitate filtration. Additional agents can include chelating agents or sequestering agents that complex the catalyst to remove it from active participation in the reaction. Agents that would form micels (i.e., small regions or particles of another liquid phase that would remove the catalyst from active participation in the reaction) to inactivate the catalyst. For example, in certain embodiments where acidic catalysts are used, the agent used to precipitate the catalyst can be sulfuric acid, phosphoric acid, sulfurous acid, $P_2O_5$, phosphorous acid, perchloric acid, hydrochloric acid, or acidic ion exchange resins. In certain embodiments where basic catalysts are used, the agent used to precipitate the catalyst can be sulfuric acid, phosphoric acid, sulfurous acid, $P_2O_5$, phosphorous acid, perchloric acid, hydrochloric acid, or acidic ion exchange resins.

In another embodiment, catalyst inactivation can be achieved by adjusting the relative solubility of the catalyst, for example, by changing the reaction mixture composition or using temperature or both to facilitate precipitation or phase transfer or both of the catalyst and/or its components. Additional solvents or other ingredients may be added to facilitate filtration or the chosen separation method (for example, lowering viscosity). Additional solvents can include, for example, hydrocarbon solvents, ethers, long chain esters, solvents that are non-polar, etc.

In a particular embodiment, wherein the reaction utilizes a copper and/or potassium acetate catalyst in an acetic acid/ hydrocarbon solvent, the catalyst may be removed by the addition of sulfuric acid in a slight molar excess to the catalyst used in the reaction mixture after the reaction is complete. The product can then be distilled at low pressure (1 mm Hg) or so. Chlorodifluoroacetic acid can be added (10 ppm) along with 1000 ppm of hydroquinone (or butylated hyroxytoluene which is by comparison more soluble). The purified product can then be distilled again at low pressure (1 mm Hg or so). Chlorodifluoroacetic acid can be added (10 ppm) along with 1000 ppm of hydroquinone (or butylated hyroxytoluene which is by comparison more soluble), either after or prior to distillation, to either the reaction mixture or the collection flask or both.

In certain embodiments, wherein the catalyst is copper acetate and potassium acetate, catalyst inactivation can be accomplished by the following procedure:

1. Paraformaldehyde is placed in toluene/acetic acid solvent with the copper acetate and potassium acetate catalysts and heated to 60° C. to produce formaldehyde and entrain it in the solvent.
2. Diethyl malonate is added gradually to the reaction mixture over a period of 30 minutes while allowing the water being formed to escape or be collected in a dean stark trap. The exotherm is observed around 80° C.-85° C. and the reaction mixture becomes transparent blue after consumption of all paraformaldehyde.
3. The reaction is allowed to continue for 60 minutes.
4. Sulfuric acid in a slight molar excess to the catalyst is added to neutralize and precipitate the catalyst and stabilize the produced methylene malonate.
5. Filtration can be done by using a glass funnel with integral fritted disc.
6. The solvent is removed by rotary evaporation under reduced pressure.
7. The methylene malonate product is collected by distillation at about 1 mm and a temperature of 60° C. and stabilized with strong acid and other traditional stabilizers in the collection flasks such that the final concentration is about (10 ppm) sulfuric acid. The purified product is then optionally distilled again at low pressure (1 mm or so). As a typical example, sulfuric acid is added (10 ppm), either after or prior to distillation, to either the reaction mixture or the collection flask or both.

Further options for catalyst inactivation could include:

1. A solvent might be used that would azeotrope the water for more rapid removal
2. With monomeric formaldehyde it might be possible to run the reaction at lower temperature.
3. Without solvent or with a higher boiling solvent higher reaction temperature would allow more rapid reaction In yet another embodiment entirely, the reaction can be conducted completely in the absence of any reaction catalyst. An advantage of this condition is the avoidance or minimization of the formation of impurities, e.g., ketals and other latent acid-forming species.

In still another embodiment, the reaction can be conducted in the presence of a reaction catalyst. An advantage of this condition is the avoidance or minimization of the formation of impurities, e.g., ketals and other latent acid-forming species.

Solvents

The present invention contemplates that the Knovenagel reaction can include a non-acidic solvent, or optionally no solvent at all.

Non-acidic solvents can include, but are not limited to, tetrahydrofuran, chloroform, dichloromethane, toluene, heptane, ethyl acetate, n-butyl acetate, dibutyl ether and hexane.

In certain other embodiment, optionally no solvent is needed. This zero-solvent approach will not only decrease the overall cost of production but will also help to lessen any negative impact on the environment caused by the methods of the invention, i.e., provides an environmentally-friendly approach to the synthesis of methylene malonates. An advantage of this condition is the avoidance or minimization of the formation of impurities, e.g., ketals and other latent acid-forming species.

In still other embodiments, the present inventors have surprisingly and unexpectedly found that the Knovenagel reaction of the invention may be conducted in the absence of both a solvent and a catalyst. Specifically, in this embodiment, the reaction can be conducted with all of the reactants added to the reaction vessel at the start of the reaction prior to adding heat and in the absence of a solvent. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Reduction of Side Products

Prior art involving the Knovenagel reaction with formaldehyde to synthesize methylene malonates typically involves using an acidic solvent, typically acetic acid, as a means of controlling the reaction parameters. Such processes, while producing methylene malonates, lead to numerous deleterious side reactions and products, including the production of ketals and other latent acid forming species between the acid solvent and the formaldehyde. The impurities can reduce monomer quality, purity and performance as a result of the later conversion of the ketals and the other latent acid forming species to acidic species, which inhibit the polymerization capacity and cure speed of the monomers, among other problems (e.g., decompose the methylene malonate esters).

In certain embodiments, the present invention includes the further step of minimizing the formation of ketals and other deleterious side products.

In one embodiment, this can be achieved by the addition of water and a medium to strong acid (i.e., an acid having a pKa range from about −8.0 to about 5.0), either organic or inorganic, to the reaction mixture to reverse the ketal formation and destroy the ketal prior to distillation or after distillation, but prior to any subsequent distillation. Water may be made present by making a solution of the acid or by direct addition. For example, this may be accomplished by adding 1% water (based on the volume of the reaction or monomer solution) or the addition of 5% sulfuric acid solution.

In another embodiment, this can be achieved by the use of a sterically hindered organic acid to reduce or eliminate ketal formation during the reaction or any subsequent heating operation. Sterically hindered organic acids can include, for example, pivalic acid. The invention is not limited to pivalic acid, however, and may include any suitable sterically hindered organic acid.

In still another embodiment, this can be achieved by the use of high enough molecular weight organic acids that formed ketals do not co-distill with the methylene malonate. High molecular weight organic acids used for this purpose can include, but are not limited to, hexanoic acid, decanoic acid, or octanoic acid, or the like.

In yet another embodiment, as noted above, the reaction may be carried out totally in the absence of any acid solvent or in the presence of a minimal amount thereof. If a minimal amount of the acid solvent is used, the acid solvent is preferably in the range of about 1-5% v/v. An advantage of this condition is the avoidance or minimization of the formation of impurities, e.g., ketals and other latent acid-forming species. Most preferably as to this embodiment, the reaction is conducted in the complete absence of any solvent.

Recovery

The present invention contemplates any suitable method for recovery of the methylene malonate products from the reaction mixtures. In certain embodiments of the present invention, the recovery method involves one or more rounds of simple distillation. In certain other embodiments, the recovery method involves one or more rounds of a rapid distillation method, e.g., flash distillation or superheat distillation. In still other embodiments, the recovery method involves a combination of one or more rounds of a rapid distillation method, e.g., flash distillation or superheat distillation, together with one or more rounds of simple distillation.

Those having ordinary skill in the art will appreciate that simple distillation methods are well known. Simple distillation is a widely used method for separating the components of a liquid mixture, e.g., reaction mixture of the present invention, and depends upon the differences in the ease of vaporization of the components, i.e., typically, the most volatile components of the liquid mixture will vaporize at the lowest temperature, whereas the least volative components will vaporize at higher temperatures. The vaporized components pass through a cooled tube or condenser causing the components to condense back into their liquid states and deposited in a collector or equivalent vessel. By separating the distillated into sequentially collected fractions ranging from most volatile to least volatile components, the components can be separated. The process can be repeated on any given fraction(s) to further separate the components.

However, as the composition of the liquid to be separated becomes more complex, the greater will be the difficulty in separating out the different volatile components therein, particularly where there is significant overlap in components having similar volatility characteristics. For instance, in the present invention, the methylene malonate products may have similar volatility characteristics as certain side products that may form, e.g., ketals, which increases the difficulty in separating those particular components.

The present invention also contemplates any scale distillation process, including laboratory scale distillation and industrial distillation processes. The main difference between laboratory scale distillation and industrial distillation is that laboratory scale distillation is often performed batch-wise, whereas industrial distillation often occurs continuously. In batch distillation, the composition of the source material, the vapors of the distilling compounds and the distillate change during the distillation. In batch distillation, a still is charged (supplied) with a batch of feed mixture (e.g., reaction mixture of the present invention), which is then separated into its component fractions which are collected sequentially from most volatile to less volatile, with the bottoms (remaining least or non-volatile fraction) removed at the end. The still can then be recharged and the process repeated. In continuous distillation, the source materials, vapors, and distillate are kept at a constant composition by carefully replenishing the source material and removing fractions from both vapor and liquid in the system. This results in a better control of the separation process. All of these methods are contemplated by the present invention.

The invention further contemplates any known improvements or modifications to simple distillation processes, including improvements to both batch and continuous distillations. For example, one improvement can include making use of a fractionating column on top of the distillation flask. The column improves separation by providing a larger surface area for the vapor and condensate to come into contact. This helps it remain at equilibrium for as long as possible. The column can even consist of small subsystems ("trays" or "dishes") which all contain an enriched, boiling liquid mixture, all with their own vapor-liquid equilibrium.

There are differences between laboratory-scale and industrial-scale fractionating columns, but the principles are the same. Examples of laboratory-scale fractionating columns (in increasing efficiency) include, for example, air condenser, vigreux column (usually laboratory scale only); packed column (packed with glass beads, metal pieces, or other chemically inert material); and spinning band distillation systems.

Further details regarding distillation processes contemplated by the present invention are as follows.

In simple distillation, the hot vapors produced are immediately channeled into a condenser that cools and condenses the vapors. Therefore, the distillate may not be pure—its composition will be identical to the composition of the vapors at the given temperature and pressure, and can be computed from Raoult's law.

As a result, simple distillation is usually used only to separate liquids whose boiling points differ greatly (e.g., by 25° C.), or to separate liquids from involatile solids or oils. For these cases, the vapor pressures of the components are usually sufficiently different that Raoult's law may be neglected due to the insignificant contribution of the less volatile component. In this case, the distillate may be sufficiently pure for its intended purpose. Keeping the above in mind, one of ordinary skill in the art will have sufficient knowledge and understanding as to utilize simple distillation where advantageous and/or desirous in the present invention as a means of separating the methylene malonate products from the reaction mixture.

Another type of general distillation method includes fractional distillation and is contemplated by the present invention. It will be appreciated that in certain situations where the boiling points of certain components in the mixture are sufficiently close to one another that Raoult's law must be taken into consideration. Therefore, fractional distillation must be used in order to sufficiently separate the components by repeated vaporization-condensation cycles within a packed fractionating column. This separation, by successive distillations, is also referred to as rectification.

As the liquid mixture to be purified (e.g., the reaction mixture of the present invention) is heated, its vapors rise into the fractionating column. As it rises, it cools, condensing on the condenser walls and the surfaces of the packing material. Here, the condensate continues to be heated by the rising hot vapors causing it to vaporize once again.

However, the composition of the fresh vapors are determined once again by Raoult's law. Each vaporization-condensation cycle (called a theoretical plate) will yield a purer solution of the more volatile component. In actual operation, each cycle at a given temperature does not occur at exactly the same position in the fractionating column. Thus, it will be appreciated that the theoretical plate is thus a concept rather than an accurate description. More theoretical plates lead to better separations. A spinning band distillation system uses a spinning band of Teflon or metal to force the rising vapors into close contact with the descending condensate, thereby increasing the number of theoretical plates.

Another type of distillation method contemplated by the present invention includes vacuum distillation. Some compounds have very high boiling points. To boil such compounds, it may be advantageous to lower the pressure at which such compounds are boiled instead of increasing the temperature. Once the pressure is lowered to the vapor pressure of the compound at the given temperature, boiling and the rest of the distillation process can commence. This technique is referred to as vacuum distillation and it is commonly found in the laboratory in the form of the rotary evaporator. This technique is also very useful for compounds which boil beyond their decomposition temperature at atmospheric pressure and which would therefore be decomposed by any attempt to boil them under atmospheric pressure. One of ordinary skill in the art will have the knowledge and understanding to apply vacuum distillation techniques when advantageous and/or where appropriate to recover the methylene malonate monomer products of the reaction.

In yet another distillation technique, named short path distillation, is a distillation technique that involves the distillate traveling a short distance, often only a few centimeters, and is normally done at reduced pressure. A typical example would be a distillation involving the distillate traveling from one glass bulb to another, without the need for a condenser separating the two chambers. This technique is often used for compounds which are unstable at high temperatures or to purify small amounts of compound. The advantage is that the heating temperature can be considerably lower (at reduced pressure) than the boiling point of the liquid at standard pressure, and the distillate only has to travel a short distance before condensing. A short path ensures that little compound is lost on the sides of the apparatus. The Kugelrohr is a kind of a short path distillation apparatus which often contain multiple chambers to collect distillate fractions. One of ordinary skill in the art will have the knowledge and understanding to apply short path distillation techniques when advantageous and/or where appropriate to recover the methylene malonate monomer products of the reaction.

Other types of known distillation techniques are also contemplated by the present invention, including, for example, the process of reactive distillation. This type of distillation involves using the reaction vessel as the still. In this process, the product is usually significantly lower-boiling than its reactants. As the product is formed from the reactants, it is vaporized and removed from the reaction mixture. This technique is an example of a continuous vs. a batch process; advantages include less downtime to charge the reaction vessel with starting material, and less workup. In addition, the method of pervaporation may be used. This method is for the separation of mixtures of liquids by partial vaporization through a non-porous membrane. Still further, the invention contemplates extractive distillation methods, which are defined as distillations that occur in the presence of a miscible, high boiling, relatively non-volatile component, i.e., the solvent, that forms no azeotrope with the other components in the mixture.

The present invention also contemplates the industrial-scale synthesis of the methylene malonates of the present invention, which can include any suitable scaled-up industrial distillation procedure and/or technology. Such technologies and methods are generally well-known in the art and can be applied and utilized to separate out the methylene malonates of the present invention by those having ordinary skill in the art without an undue amount of experimentation. Large scale industrial distillation applications can include both batch and continuous fractional, vacuum, azeotropic, extractive, and steam distillation methods.

Industrial distillation is typically performed in large, vertical cylindrical columns known as distillation towers or distillation columns with diameters ranging from about 65 centimeters to 16 meters and heights ranging from about 6 meters to 90 meters or more. When the process feed (e.g., a methylene malonate reaction mixture of the invention) has a diverse composition, as in distilling crude oil, liquid outlets at intervals up the column allow for the withdrawal of different fractions or products having different boiling points or boiling ranges. The "lightest" products (those with the lowest boiling point) exit from the top of the columns and the "heaviest" products (those with the highest boiling point) exit from the bottom of the column. One of ordinary skill in the art will have the knowledge and understanding to apply such industrial distillation techniques when advantageous and/or where appropriate to recover the methylene malonate monomer products of the reaction of the invention.

In one preferred embodiment, the present invention contemplates utilizing the technique referred to as flash distillation in the separation of methylene malonate products from the reaction mixture of the invention. It will be appreciated that distillation is a widely used industrial method for separating liquid mixtures and is at the heart of the separation processes in many chemical processes. The most elementary form of the method is simple distillation—as discussed above—in which the liquid is brought to boiling and the vapor formed is separated and condensed to form a product.

It has been surprisingly discovered that the application of flash distillation eliminates or minimizes the formation of undesirable side reaction products and/or unwanted intermediate and product polymer complexes. By comparison, the prior art typically conducted bulk liquid phase reactions for the Knovenagel synthesis of methylene malonates. Such systems have the disadvantage of intimate molecular contact once the methylene malonate forms and before that allows for a multitude of competing reactions to occur based upon the byproducts of the optional acid solvent, the formaldehyde, the product of formaldehyde and water (methylene glycol), the methylene malonate, the created water and any effects of any catalyst system, if present. Even further, the inventors have discovered through NMR studies that methods that utilize a liquid phase Knovenagel reaction do not in fact produce monomer, but rather monomer that almost instantaneously forms a type of polymer complex—not likely through the double bond—that must be subsequently "cracked" (i.e., reduced to monomer units) or otherwise reversed. In other words, no exo- or $CH_2$-containing double bonds are detectable following a prior art Knovenagel reaction. It would be preferred to not go through an energy intensive step with prolonged heating times that produces a myriad of potential deleterious products that reduce yields and affect monomer activity and purification methodology.

It is further contemplated that monomer obtained by the methods of the invention may be further redistilled at least once, twice, or thrice or more additional times to further fractionate the methylene malonate monomer product. Preferably, these redistillations should be conducted very quickly following the flash or superheat distillation process, preferably no more than about 1 minute, or about 10 minutes, or about 30 minutes, or about 45 minutes, or about 60 minutes, or about 2 hours, or about 4 hours, or about 12 hours, or about 24 hours. More preferably, the follow-on distillations occurs no more than about 60 minutes after the initial flash or superheat distillation method. The inventors have surprisingly found that the redistillation following the recovery facilitates the elimination or minimization of the unwanted deleterious side products and the formation of undesirable polymer complexes that impinge on the overall quality and reactivity of the methylene malonate monomers.

In this aspect of the invention, flash distillation, superheat distillation or any other suitable high-temperature distillation process can be utilized to effectively eliminate or minimize the formation of undesirable polymer complex intermediates and/or products and other deleterious side products. Flash distillation involves using high temperatures—typically above the boiling point of the methylene malonate at atmospheric pressure or somewhat below that—to prevent and minimize such side reactions and/or the formation of such polymer complexes. Specifically, the effect of flash distillation is to prevent the intimate contact required to accelerate these side reactions and polymer complex formations by simultaneous distillation and condensing of the final products to an ambient temperature or any temperature at which the materials do not react. In one aspect, as in any aspect of distillation, the distillate reaction product fractions can be distilled and condensed into a stabilized system that inhibits the polymerization and degradation of the monomer product, such as, an acid stabilizer.

To conduct the flash distillation technique of the invention, the reaction can be conducted in a first reaction vessel. Specifically, the technique may proceed by
(a) reacting a malonic acid ester with a source of formaldehyde; optionally in the presence of an acidic or basic catalyst; and optionally in the presence of an acidic or non-acidic solvent, to form a methylene malonate monomer in a reaction mixture; and
(b) recovering the methylene malonate monomer from the reaction mixture by:
1) addition of the reaction mixture to a heat transfer agent;
2) introducing the reaction mixture into to a flash distillation chamber; or
3) introducing the reaction mixture to a surface of a heat exchanger;
wherein the heat transfer agent, the flash distillation chamber or the heat exchanger is heated to between about 200° C. and about 220° C.;
to produce a flash distillate of the methylene malonate monomer; and collecting the distillate of the methylene malonate monomer.

Immediately upon completion of the reaction, e.g., at regular intervals or the like, the reaction mixture (having already formed at least some of the methylene malonate product) is transferred into a flash distillation chamber or another vessel that contains a heat transfer media, such as, for example, a solid particulate like silica gel or sand or a liquid, such as a silicone oil, or a heat exchanger, which very rapidly heats the reaction mixture, vaporizing the components and sending them through the condenser to be condensed.

Any heat transfer agent which will not result in the production of deleterious side products may be used as will be known by one of skill in the art. In certain embodiments of the invention wherein a heat transfer agent is utilized, the heat transfer agent is one or more metal beads, one or more glass beads, one or more porcelain beads, silica, silicone oil, mineral oil, a petroleum based heat transfer oil or a synthetic chemical based heat transfer oil.

Any heat exchanger which will not result in the production of deleterious side products may be used as will be known by one of skill in the art. another embodiment of the invention wherein a heat exchanger is used, the heat exchanger is a shell and tube heat exchanger, a plate heat exchanger, and adiabatic wheel heat exchanger, a finned pipe heat exchanger, a plate fin heat exchanger, or a scraped surface heat exchanger.

In certain embodiments of the invention the reacting step (a) is performed at about 60° C. to about 130° C.

This process could be run as a batch reaction or as a continuous reaction, in both cases with a continuous flow of ingredients. Surprisingly, the primary product produced via this approach is methylene malonate with the remainder typically unreacted formaldehyde and malonate, both of which can be recovered and recycled.

A variation of the flash distillation, referred to herein as the superheat distillation reaction, is also contemplated whereby the heat transfer media is contained within the reaction mixture. Specifically, the technique may proceed by:
(a) reacting a malonic acid ester with a source of formaldehyde in the presence of a heat transfer agent; optionally in the presence of an acidic or basic catalyst; and optionally in the presence of an acidic or non-acidic solvent, to form a methylene malonate monomer in a reaction mixture; and
(b) recovering the methylene malonate monomer from the reaction mixture by heating the reaction mixture to between about 200° C. and about 220° C. to produce a distillate of the methylene malonate monomer; and collecting the distillate of the methylene malonate monomer.

Once the reaction has been allowed to proceed and at least some of the methylene malonate product has formed, the reaction mixture is heated. Due to the presence of the heat transfer media, the heat transfer media facilitates rapid transfer of heat to the reaction mixture, thereby vaporizing the components and sending them through the condenser to be condensed. This process could be run as a batch reaction or as a continuous reaction, in both cases with a continuous flow of ingredients. Surprisingly, the primary product produced via this approach is methylene malonate with the remainder typically unreacted formaldehyde and malonate, both of which can be recovered and recycled.

In certain embodiments of the invention wherein a heat transfer agent is utilized, the heat transfer agent is one or more metal beads, one or more glass beads, one or more porcelain beads, silica, silicone oil, mineral oil, a petroleum based heat transfer oil or a synthetic chemical based heat transfer oil.

It is further contemplated that the distillate formed by the flash distillation or the superheat distillation methods by further distilled at least once, twice, or thrice or more additional times to further fractionate the methylene malonate monomer product. Preferably, these refractionations should be conducted very quickly following the flash or superheat distillation process, preferably no more than about 1 minute, or about 10 minutes, or about 30 minutes, or about 45 minutes, or about 60 minutes, or about 2 hours, or about 4 hours, or about 12 hours, or about 24 hours. More preferably, the follow-on distillations occurs no more than about 60 minutes after the initial flash or superheat distillation method. The inventors have surprisingly found that the redistillation following the flash and/or superheat distillation facilitates the elimination or minimization of the unwanted deleterious side products and the formation of undesirable polymer complexes that impinge on the overall quality and reactivity of the methylene malonate monomers.

Yet another type of suitable recovery method can be by sublimation. Some substances can pass directly from the solid to the gaseous stage without first melting and becoming liquid. These substances are said to be able to sublimate. Substances that sublimate, when mixed with substances that do not sublimate, can be separated by heating the mixture until the substance that can sublime is completely gone. In sublimation, a solid compound evaporates directly to the gas phase without becoming a liquid. In vacuum sublimation, the sample is placed under reduced pressure which permits sublimation at lower temperatures (which can mean less decomposition in a sample). In purification by sublimation, a solid compound is heated and evaporates. The vapors condense on a cold surface to form new crystals. Sublimation can be a suitable means in the present invention to purify samples of methylene malonate monomers, and in particular, those that are first crystallized to a solid. Methods for separation and recovery by sublimation are well-known in the art. A resource for carrying out sublimation recovery can be found, for example, in *Crystallization*, Publ. Butterworth-Heinemann, 2001, By John William Mullin, Chapter 8.3.2, page 363, the relevant contents of which are incorporated herein by reference.

Recrystallization is another suitable means for recovering the methylene malonate monomer products of the invention. The general principle is that the methylene malonate monomer products and any impurities therein may be dissolved in a solvent and then cooled to produce a fresh crop of purer crystals of methylene malonate monomers, provided that the impurities are more soluble in the solvent than the main product. This process may be repeated a multitude of times until a pure crystal of the main product may be obtained. The techniques of recrystallization will be well-known in the art, but further details may be found in *Crystallization*, Publ. Butterworth-Heinemann, 2001, By John William Mullin, Chapter 7.1, page 289, the relevant contents of which are incorporated herein by reference.

Any of the recovery techniques described herein may be conducted in isolation or in any combination where suitable.

As mentioned, distillation and other separation methods are well-known in the art. Further exemplary methods of distillation contemplated by the present invention, including simple distillation methods, batch and industrial distillation processes, and flash and superheat distillation methods, as well as other mentioned above, can be found, for example, in U.S. Pat. No. 7,771,567 (Salt water distillation system); U.S. Pat. No. 7,649,108 (Process for the distillation of a mixture of isomeric diisocyanatodiphenylmethanes); U.S. Pat. No. 7,610,775 (Distillation process using microchannel technology); U.S. Pat. No. 7,603,889 (System for monitoring and controlling unit operations that include distillation); U.S. Pat. No. 7,305,850 (Distillation process using microchannel technology); U.S. Pat. No. 6,936,140 (Water distillation system); U.S. Pat. No. 6,841,064 (Process for the gentle flash distillation of residual oils); U.S. Pat. No. 6,716,355 (Method for the purification of a liquid by membrane distillation, in particular for the production of desalinated water from seawater or brackish water or process water); U.S. Pat. No. 6,413,415 (Method for high-temperature short-time distillation of residual oils); U.S. Pat. No. 6,291,703 (Preparation of substituted hydroxyhydrocinnamate esters by continuous transesterification using reactive distillation); U.S. Pat. No. 5,284,987 (Preparation of a dimethyltetralin in a distillation reactor); U.S. Pat. No. 5,227,027 (High efficiency water distillation apparatus using a heat pump system and process for use thereof); U.S. Pat. No. 5,064,507 (Distillation process for recovery of to high purity phenol); U.S. Pat. No. 4,783,242 (Distillation system and process); U.S. Pat. No. 4,767,503 (Removal of light impurities from caprolactam by distillation with water); H214 (Distillation process for the isolation of 1,1-difluoro(mono- or dihalo) ethoxy-benzeneamines); U.S. Pat. No. 4,584,064 (Device and installations for the distillation by thin layer evaporation particularly of hydrocarbons, and process for operating this device); U.S. Pat. No. 4,450,067 (Distillation-induced extraction process); U.S. Pat. No. 4,440,601 (Method and apparatus for high volume fractional distillation of liquids); U.S. Pat. No. 4,411,740 (Separation of chlorosilanes by extractive distillation); U.S. Pat. No. 4,319,964 (Apparatus for high volume distillation of liquids); U.S. Pat. No. 4,282,071 (Anhydrous separation of volatile aluminum chloride complex from an ethylbenzene production stream by distillation); U.S. Pat. No. 4,282,067 (Apparatus for high volume distillation of liquids); U.S. Pat. No. 4,243,493 (Process for transportation and distillation of petroleum with methanol); U.S. Pat. No. 4,236,975 (Recovery of methyl heptafluorobutyrate from water by distillation); U.S. Pat. No. 4,229,263 (Recovery of methyl heptafluorobutyrate from methanol by distillation); U.S. Pat. No. 4,224,112 (Recovery of 1,1-dihydroheptafluorobutanol from water by distillation); U.S. Pat. No. 4,186,060 (Method and apparatus for high volume distillation of liquids); U.S. Pat. No. 4,186,058 (Method and apparatus for high volume distillation of liquids); U.S. Pat. No. 4,176,012 (Adjacent loop distillation); U.S. Pat. No. 4,148,693 (Horizontal cylindrical distillation apparatus); U.S. Pat. No. 4,140,584 (Distillation plant); U.S. Pat. No. 4,035,243 (Method and apparatus for high volume distillation of liquids); U.S. Pat. No. 4,018,656 (Thermal softening and distillation by regenerative method); U.S. Pat. No. 4,004,984 (Distillation plant); U.S. Pat. No. 4,001,345 (Distillation of methylchloroform); U.S. Pat. No. 3,966,562 (Multi-stage flash distillation plant); U.S. Pat. No. 3,945,891 (Distillation process for purification of triaryl phosphate esters), each of the above of which are incorporated in their entireties by reference herein.

Compositions

The methylene malonate monomers of the invention can be incorporated into any number of compositions and products including but not limited to monomer-based compositions, oligomer-based compositions and polymer based compositions.

Such monomer-based and oligomer-based compositions include, but are not limited to an adhesive, a coating, a sealant, a composite, or a surfactant.

Such polymer-based compositions include, but are not limited to, a sealant, a thermal barrier coating, a textile fiber, a water-treatment polymer, an ink carrier, a paint carrier, a packaging film, a molding, a medical polymer, a polymer film, a polymer fiber or a polymer sheet.

In each case, the compositions of the invention may be formulated to include one or more materials to extend the shelf-life as well as control the onset of cure of the materials. In certain embodiments, the compositions are formulated such that the composition is stable for at least 1 month, or for at least 2 months, or for at least 3 months, or for at least 4 months, or for at least 5 months, or for at least 5-10 months, or for at least 10-20 months, or for at least 20-30 months. Preferably, the adhesive composition comprising the methylene malonate monomers of the invention, or other commercial compositions or products, are stable for at least one year.

Such formulation materials include acidic stabilizer, volatile acid stabilizers, acidic gases, free radical stabilizers, sequestering agents, cure accelerators and rheology modifiers.

The present invention contemplates any suitable acidic stabilizer known in the art, including, for example, trifluoromethane sulfonic acid, chlorodifluoro acid, maleic acid, methane sulfonic acid, difluoro acetic acid, trichloroacetic acid, phosphoric acid, dichloroacetic acid or like acid. Acidic stabilizers can include any material which can be added to the monomer or polymer compositions to extend shelf-life, e.g., by up to, for example, 1 year or more. Such acidic stabilizers may have a pKa in the range of, for example, between about −15 to about 5, or between about −15 to about 3, or between about −15 to about 1, or between about −2 to about 2, or between about 2 to about 5, or between about 3 to about 5.

Volatile acid stabilizers include any material which can be added to the monomer or polymer compositions to extend shelf-life and stabilize the vapor phase above the composition upon storage, e.g., acidic gases. Such volatile acid stabilizers may have a boiling point, for example, less than about 200° C.; less than about 170° C.; or less than about 130° C.

Acidic gases include any gaseous material which can be added to the monomer or polymer compositions to extend shelf-life and stabilize the vapor phase above the composition upon storage. Such acid gases can include, but are not limited to, $SO_2$ or $BF_3$.

For each of these acidic stabilizing materials, such acidic stabilizer can be present in a concentration of about 0.1 ppm to about 100 ppm, about 0.1 ppm to about 25 ppm; or about 0.1 ppm to about 15 ppm.

Free radical stabilizers can include any material capable of stabilizing or inhibiting free radical polymerization of the material upon standing In one embodiment, the free radical stabilizers are phenolic free radical stabilizers such as, HQ (hydroquinone), MEHQ (methyl-hydroquinone), BHT (butylated hydroxtoluene) and BHA (butylated hydroxyanisole). In certain embodiments, the free radical stabilizers are present in a concentration of 0.1 ppm to 10,000 ppm; 0.1 ppm to 3000 ppm; or 0.1 ppm to 1500 ppm. In certain other embodiments, particularly where a free radical or ultraviolet cure will be utilized on the materials of the invention, the free radical stabilizers are present in a concentration of 0.1 ppm to 1000 ppm; 0.1 ppm to 300 ppm; or 0.1 ppm to 150 ppm.

Sequestering agents include any material capable of enhancing the bonding of materials containing acid salts such as paper or wood. Such sequestering agents include, but are not limited to crown ethers, silyl crowns, calixarenes and polyethylene glycols. Sequestering agents also enhance the utility of surface accelerators that are acid salts applied to surfaces to control the rate of cure of the materials.

Cure accelerators include any material capable of speeding the rate of cure of the methylene malonate monomers of the invention. Such cure accelerators include but are not limited to sodium or potassium acetate; acrylic, maleic or other acid salts of sodium and potassium; salts such as tetrabutyl ammonium fluoride, chloride, or hydroxide; or chemically basic materials such as amines and amides, or salts of polymer bond acids. Such cure accelerators can be added directly to the compositions of the invention or applied to the material to be bonded prior to addition of the composition of the invention.

Rheology modifiers include any material which can modify the viscosity of the compositions of the invention as well as thixotropic properties for greater utility in certain applications. Rheology modifiers include, but are not limited to, hydroxyethylcellulose, ethyl hydroxyethylcellulose, methylcellulose, polymeric thickeners, pyrogenic silica or a combination thereof. Rheology modifiers also include, but are not limited to, commercial tougheners such as thermoplastic elastomer, such as a styrenic block copolymer.

The methylene malonate-containing compositions of the invention may also optionally include other additives, such as plasticizing agents, thixotropic agents, natural or synthetic rubbers, filler agents, and reinforcing agents, etc. Such additives are well known to those skilled in the art.

The methylene malonate-containing compositions of the invention may optionally include at least one plasticizing agent that imparts flexibility to the polymer formed from the methylene malonate monomer. The plasticizing agent preferably contains little or no moisture and should not significantly affect the stability or polymerization of the monomer. Such plasticizers are useful in polymerized compositions to be used in any application in which flexibility of the adhesive or polymer product is desirable.

Examples of suitable plasticizers include, without limitation, acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts less than about 60 weight %, or less than about 50 weight %, or less than about 30 weight %, or less than about 10 weight %, or less than about 5 weight %, or less than about 1 weight % or less, provides increased film strength (e.g., toughness) of the polymerized monomer over polymerized monomers not having plasticizing agents.

The methylene malonate-containing compositions of the invention may also optionally include at least one thixotropic agent, i.e., the property of exhibiting a high fluidity during deformation by force of a sprayer, roller or trowel, but losing the fluidity when left at rest. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513 or 4,510,273, the disclosures of which are hereby incorporated in their entireties.

The methylene malonate-containing compositions of the invention may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The methylene malonate-containing compositions of the invention may also optionally comprise one or more other reinforcing agents (e.g., fibrous reinforcements) other than natural or synthetic rubber to impart impact resistance and/or to impart structural strength or to provide shape or form. Examples of such agents are well known in the art. Examples of suitable fibrous reinforcement include PGA microfibrils, collagen microfibrils, cellulosic microfibrils, and olefinic microfibrils. The compositions may also contain colorants such as dyes (e.g., neutral), pigments, and pigment dyes. Examples of suitable colorants include 6-hydroxy-5-[(4-sulfophenyl)axo]-2-naphthalene-sulfonic acid (FD+C Yellow No. 6); 9-(o-carboxyphenOyl)-6-hydroxy-2,4,5,7-tetraiodo-3H-xanthen-3-one monohydrate (FD+C Red No. 3); and 2-(1,3-dihydro-3-oxo-5-sulfo-2H-indol-2-ylidene)-2,3-dihydro-3-oxo-1H-indole-5-sulfonic acid (FD+C Blue No. 2), wherein the suitable colorant should not destabilize the monomer.

The methylene malonate-containing compositions of the invention may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the methylene malonate-containing compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such crosslinking agents.

Other compositions and additives contemplated by the present invention, including additional stabilizers, accelerators, plasticizers, fillers, opacifiers, inhibitors, thixotrophy conferring agents, dyes, fluorescence markers, thermal degradation reducers, adhesion promoters, thermal resistance conferring agents and combinations thereof, and the like, some of which are exemplified by U.S. Pat. Nos. 5,624,669; 5,582,834; 5,575,997; 5,514,371; 5,514,372; 5,312,864 and 5,259,835, the disclosures of all of which are hereby incorporated in their entirety by reference.

Depending on whether the composition is a monomer-based composition (e.g., inks, adhesives, coatings, sealants or reactive molding) or a polymer-based composition (e.g., fibers, films, sheets, medical polymers, composite polymers and surfactants), one having ordinary skill in the art will have the knowledge and skill by which to formulate such compositions and/or products without undue experimentation having suitable amounts, levels and combinations of the above types of additives and components.

The above disclosure generally describes the present invention. A more complete understanding can be obtained by reference to the following specific examples, which are provided for purposes of illustration only and are not intended to limit the scope of the invention.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

The following examples illustrate various exemplary embodiments of the methods described in this disclosure.

Analytical Methods

The structures of monomers of this invention were confirmed using one or more of the following procedures.

NMR

Routine one-dimensional NMR spectroscopy was performed on either a 400 MHz Varian® spectrometer or a 400 MHz Bruker® spectrometer. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for 1H spectra.

GC/MS

Electron impact mass spectra (EI-MS) were obtained with a Hewlett Packard 5970 mass spectrometer equipped Hewlett Packard 5890 Gas Chromatograph with. The ion source was maintained at 270° C.

ABBREVIATIONS AND ACRONYMS

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

| | |
|---|---|
| atm | atmosphere |
| br s | broad singlet |
| C | Celsius |
| d | doublet |
| dd | doublet of doublets |
| MM | methylene malonate |
| HQ | hydroquinone |
| GC-MS | Gas Chromatograph mass spectroscopy |
| g | gram |
| h | hour, hours |
| 1H NMR | proton nuclear magnetic resonance |
| J | coupling constant (NMR spectroscopy) |
| L | liter |
| M | mol L-1 (molar) |
| m | multiplet |
| MHz | megahertz |
| min | minute, minutes |
| mL | milliliter |
| mM | micromolar |
| mol | mole |
| MS | mass spectrum, mass spectrometry |
| m/z | mass-to-charge ratio |
| N | equivalents L-1 (normal) |
| NMR | Nuclear Magnetic Resonance |
| pH | negative logarithm of hydrogen ion concentration |
| q | quartet |
| rt | room temperature |
| s | singlet |
| t | triplet |

Example 1

Non-Acidic Solvents with Basic Catalyst with the Dropwise Addition of Diethyl Malonate 1. In a two-liter 3-neck round bottom flask (equipped with a condenser), 30 g of paraformaldehyde (1 mol), 5 g of potassium acetate and 5 g of copper (II) acetate were mixed in 40 ml of tetrahydrofuran (THF).
2. This mixture was stirred and heated at 65° C. for 40 min. From an additional funnel, 80 g (0.5 mol) of diethyl malonate (DEM) was then added dropwise to the reaction mixture.
3. At the end of the addition of DEM (about an hour), the reaction mixture was further stirred at 65° C. for 2 hours.
4. The reaction mixture was then cooled to room temperature and 5 g of sulfuric acid was added into the flask with stirring.
5. The precipitates were then removed by filtration and the filtrate was collected. 0.08 g (1000 ppm) of hydroquinone (HQ) and 0.08 g of sulfuric acid (1000 ppm) were added to the collected filtrate.
6. The filtrate was then distilled at reduced pressure. Diethyl Methylenemalonate was collected at 55-70° C. with about 1.5 mm Hg of vacuum as the crude monomer.
7. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum
8. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 2

Non-Acidic Solvents with Basic Catalyst with all Reagents Added all at the Same Time 1. In a two-liter 3-neck round bottom flask (equipped with a condenser), 30 g of paraformaldehyde (1 mol), 80 g (0.5 mol) of diethyl malonate (DEM), 5 g of potassium acetate and 5 g of copper (II) acetate were mixed in 40 ml of tetrahydrofuran (THF).
2. This mixture was stirred and heated at 65° C. for 3 hours.
3. The reaction mixture was then cooled to room temperature and 5 g of sulfuric acid was added into the flask with stirring.
4. The precipitates were then removed by filtration and the filtrate was collected. 0.08 g (1000 ppm) of hydroquinone (HQ) and 0.08 g of sulfuric acid (1000 ppm) were added to the collected filtrate.
5. The filtrate was then distilled at reduced pressure. Diethyl Methylenemalonate was collected at 55-70° C. with about 1.5 mm Hg of vacuum as the crude monomer.
6. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
7. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 3

Non-Acidic Solvents with Basic Catalyst. Addition of Paraformaldehyde to the Reaction Mixture 1. The 3-neck round bottom flask, with a magnetic stir bar inside, was first dried to make it moisture free, fitted with thermometer and the Dean Stark apparatus connected with a condenser.
2. The reaction solvent, 40 mL of tetrahydrofuran (THF) is then transferred to the RBF. 80 mL of Diethylmalonate (DEM) (0.5 moles), 3 gm of Cu(OAc)$_2$ monohydrate (0.015 moles), 3 gm of Potassium Acetate were all added to the reaction medium sequentially.
3. The initial color of the reaction mixture was blulish-green. The reaction mixture was then heated up to 65 Deg C. for 30 mins.
4. After heating 15 gm of Paraformaldehyde was added over a period of 15 mins. After adding the Paraformaldehyde, N$_2$ gas was bubbled through the reaction mixture to remove the water from the reaction mixture.
5. Removal of water was very crucial because the overall reaction rate slowed down drastically in case of larger scale.
6. The reaction progress was monitored by using GC/MS by taking the aliquot after 1 hr. Based on the unreacted DEM, usually another 10-15 gm of Paraformaldehyde was added for 90-95% conversion of DEM. It was observed that the reaction medium changes color gradually to lighter-bluish green after addition of Paraformaldehyde.
7. After 5.5 hrs of reaction the heating is switched off and once cooled, ~3 gm of H$_2$SO$_4$ was added to the reaction mixture to neutralize the basic catalyst as well as Potassium Acetate.
8. The very light blue color of the reaction mixture indicates the optimum neutralization. After neutralization the salt was the filtered off
9. The filtrate was then set to rotovap under vacuum for evaporating the Toluene/Acetic Acid solvent. Removal of Acetic Acid is crucial because presence of Acetic Acid could increase the curing time of the monomer at parts per million quantities as well as initiate corrosion of metal containing substrates.
10. After that 0.25 g (1000 ppm) of hydroquinone (HQ) and 0.25 g of sulfuric acid (1000 ppm) were added to the collected filtrate.
11. 1$^{st}$ distillation: the filtrate was then distilled at reduced pressure to remove acetic acid. Diethyl Methylenemalonate was collected at 55-70° C. with about 1.5 mm Hg of vacuum as the crude monomer.
12. 2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 4

Solventless with Basic Catalyst

1. To a 3-neck, round bottom flask equipped with thermocouple, mechanical stirrer, and nitrogen blanket, is charged 120 g (0.75 moles) of diethylmalonate (DEM).
2. With stirring, 45 g (1.5 moles) of paraformaldehyde was added. In addition, the catalyst system consists of 1 gm (0.73 mol %) of copper (II) acetate with 2 gms (2.7 mol %) of potassium acetate, based on DEM, was lastly added.
3. The reaction mixture was heated slowly to ~60° C. whereby an exotherm to 110-115 C occurs.
4. The temperature of the resulting reaction mixture was maintained at 85° C. for 30 minutes.
5. The reaction mixture was then filtered through silica plug to remove catalysts and the filtrate was collected.
6. The filtrate was stabilized by sulfuric acid and hydroquinone.
7.7. The filtrate was then distilled at reduced pressure. Diethyl Methylenemalonate was collected at 55-70° C. with about 1.5 mm Hg of vacuum as the crude monomer.
8. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
9. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 5

Non-Acidic Solvents with Acidic Catalyst with the Dropwise Addition of Diethyl Malonate 1. In a two-liter 3-neck round bottom flask (equipped with a condenser), 30 g of paraformaldehyde (1 mol) and 7 g of zinc chloride were mixed in 40 ml of tetrahydrofuran (THF).
2. This mixture was stirred and heated at 65° C. for 40 min. From an additional funnel, 80 g (0.5 mol) of diethyl malonate (DEM) was then added dropwise to the reaction mixture.
3. At the end of the addition of DEM (about an hour), the reaction mixture was further stirred at 65° C. for 2 hours.
4. The reaction mixture was then cooled to room temperature and 7 g of sulfuric acid was added into the flask with stirring.
5. The precipitates were then removed by filtration and the filtrate was collected. 0.08 g (1000 ppm) of hydroquinone (HQ) and 0.08 g of sulfuric acid (1000 ppm) were added to the collected filtrate.
6. The filtrate was then distilled at reduced pressure. Diethyl Methylenemalonate was collected at 55-70° C. with about 1.5 mm Hg of vacuum as the crude monomer.
7. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
8. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 6

Non-Acidic Solvents with Acidic Catalyst. Reagents Added all at the Same Time

1. In a two-liter 3-neck round bottom flask (equipped with a condenser), 80 g (0.5 mol) of diethyl malonate (DEM), 30 g of paraformaldehyde (1 mol) and 7 g of zinc chloride were mixed in 40 ml of tetrahydrofuran (THF).
2. This mixture was stirred and heated at 65° C. for 3 hours.
3. The reaction mixture was then cooled to room temperature and 7 g of sulfuric acid was added into the flask with stirring.
4. The precipitates were then removed by filtration and the filtrate was collected. 0.08 g (1000 ppm) of hydroquinone (HQ) and 0.08 g of sulfuric acid (1000 ppm) were added to the collected filtrate.
5. The filtrate was then distilled at reduced pressure. Diethyl Methylenemalonate was collected at 55-70° C. with about 1.5 mm Hg of vacuum as the crude monomer.
6. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
7. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 7

Non-Acidic Solvents with Acidic Catalyst. Addition of Paraformaldehyde to the Reaction Mixture The 3-neck RBF, with a magnetic stir bar inside, was first dried to make it moisture free, fitted with thermometer and the Dean Stark apparatus connected with a condenser.

1. 40 mL of THF, 80 mL of Diethylmalonate (DEM) (0.5 moles) and 3.4 gm of ZnCl2 (0.025 moles) were taken in a 3 neck RBF.
2. The initial color of the reaction mixture was milky white. The reaction mixture was then heated up to 65 Deg C. for 30 mins.
3. After heating 15 gm of paraformaldehyde was added over a period of 15 mins. After adding the paraformaldehyde, N$_2$ gas was bubbled through the reaction mixture to remove the water from the reaction mixture.
4. Removal of water was very crucial because the overall reaction rate slowed down drastically in case of larger scale.
5. The reaction progress was monitored by using GC/MS by taking the aliquot after 1 hr. Based on the unreacted DEM, usually another 5-10 gm of Paraformaldehyde was added for 90-95% conversion of DEM.
6. After 5.5 hrs of reaction the heating is switched off and once cooled, ~3 gm of H$_2$SO$_4$ was added to the reaction mixture to neutralize the basic catalyst as well as Potassium Acetate.
7. The transparent reaction mixture indicates the optimum neutralization. After neutralization the salt was the filtered off.
8. The filtrate was then set to rotovap under vacuum for evaporating the Toluene/Acetic Acid solvent. Removal of Acetic Acid was crucial because presence of Acetic Acid could increase the curing time of the monomer even though the GC is showing 98-99% purity.
9. After that 0.25 g (1000 ppm) of hydroquinone (HQ) and 0.25 g of sulfuric acid (1000 ppm) were added to the collected filtrate.
10. 1$^{st}$ distillation: the filtrate was then distilled at reduced pressure to remove acetic acid. Diethyl Methylenemalonate was collected at 55-70° C. with about 1.5 mm Hg of vacuum as the crude monomer.
11. 2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 8

Solventless with Acidic Catalyst, Reagents Added all at the Same Time

1. In a two-liter 3-neck round bottom flask (equipped with a condenser), 80 g (0.5 mol) of diethyl malonate (DEM), 30 g of paraformaldehyde (1 mol) and 7 g of zinc chloride were mixed together.
2. This mixture was stirred and heated at 65° C. for 1 hour.

3. The reaction mixture was then cooled to room temperature and 7 g of sulfuric acid was added into the flask with stirring.
4. The precipitates were then removed by filtration and the filtrate was collected. 0.08 g (1000 ppm) of hydroquinone (HQ) and 0.08 g of sulfuric acid (1000 ppm) were added to the collected filtrate.
5. The filtrate was then distilled at reduced pressure. Diethyl Methylenemalonate was collected at 55-70° C. with about 1.5 mm Hg of vacuum as the crude monomer.
6. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
7. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 9

Solventless with Acidic Catalyst. Addition of Paraformaldehyde to the Reaction Mixture The 3-neck RBF, with a magnetic stir bar inside, was first dried to make it moisture free, fitted with thermometer and the Dean Stark apparatus connected with a condenser.
1. 80 mL of Diethylmalonate (DEM) (0.5 moles) and 3.4 gm of ZnCl2 (0.025 moles) were taken in a 3 neck RBF.
2. The initial color of the reaction mixture was milky white. The reaction mixture was then heated up to 65° C. for 30 mins.
3. After heating 15 gm of paraformaldehyde was added over a period of 15 mins. After adding the paraformaldehyde, N$_2$ gas was bubbled through the reaction mixture to remove the water from the reaction mixture.
4. Removal of water was very crucial because the overall reaction rate slowed down drastically in case of larger scale.
5. The reaction progress was monitored by using GC/MS by taking the aliquot after 1 hr. Based on the unreacted DEM, usually another 5-10 gm of Paraformaldehyde was added for 90-95% conversion of DEM.
6. After 5.5 hrs of reaction the heating is switched off and once cooled, ~3 gm of H$_2$SO$_4$ was added to the reaction mixture to neutralize the basic catalyst as well as Potassium Acetate.
7. The transparent reaction mixture indicates the optimum neutralization. After neutralization the salt was the filtered off.
8. The filtrate was then set to rotovap under vacuum for evaporating the Toluene/Acetic Acid solvent. Removal of Acetic Acid was crucial because presence of Acetic Acid could increase the curing time of the monomer even though the GC is showing 98-99% purity.
9. After that 0.25 g (1000 ppm) of hydroquinone (HQ) and 0.25 g of sulfuric acid (1000 ppm) were added to the collected filtrate.
10. 1$^{st}$ distillation: the filtrate was then distilled at reduced pressure to remove acetic acid. Diethyl Methylenemalonate was collected at 55-70° C. with about 1.5 mm Hg of vacuum as the crude monomer.
11. 2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 10

General Procedure for Synthesis of Methylene Malonate

In a two-liter 3-neck round bottom flask (equipped with a condenser, thermal couple and additional funnel), 30 g of paraformaldehyde (1 mol), 5 g of potassium acetate and 5 g of copper (II) acetate were mixed in 200 ml of acetic acid. This mixture was stirred and heated at 85° C. for 40 min. From additional funnel, 80 g (0.5 mol) of diethyl malonate (DEM) was then added drop-wise to the reaction mixture. At the end of the addition of DEM (about an hour), the reaction mixture was further stirred at 85° C. for 2 hours.

The reaction mixture was then cooled to room temperature and 5 g of sulfuric acid was added into the flask with stirring. The precipitates were then removed by filtration and the filtrate was collected. 0.25 g (1000 ppm) of hydroquinone (HQ) and 0.25 g of sulfuric acid (1000 ppm) were added to the collected filtrate.

Purification of Monomer

1$^{st}$ distillation: the filtrate was then distilled at reduced pressure to remove acetic acid. Diethyl Methylenemalonate was collected at 55-70° C. with about 1.5 mm Hg of vacuum as the crude monomer.

2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10 ppm of chlorodifluoroacetic acid.

TABLE 1

| | | | Reactions for preparing Diethyl Methylenemalonate | | | | |
|---|---|---|---|---|---|---|---|
| Example 1 | Temp (° C.) | DEM (gram) | KOAc: Cu(OAc)$_2$ (gram:gram) | CH$_2$O (gram) | AcOH (ml) | % Crude Yield (GC-MS) | % Distillation Yield |
| Batch 1 | 85 | 80 | 5:5 | 30 | 200 | 75 | 46 |
| Batch 2 | 85 | 80 | 5:5 | 30 | 200 | 72 | 42 |
| Batch 3 | 85 | 80 | 5:5 | 30 | 200 | 74 | 45 |

Figure 11:
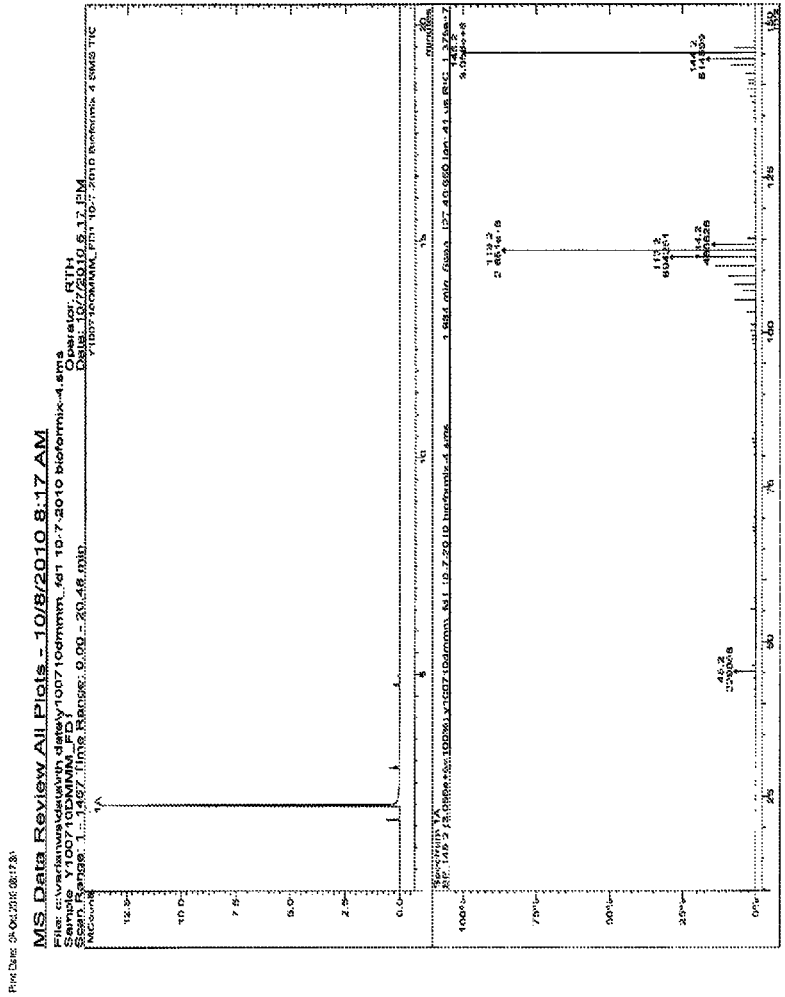
FIG. 11 provides a GC-MS spectrum of crude dimethyl methylene malonate monomer containing water, formaldehyde and other impurities.
Figure 12:
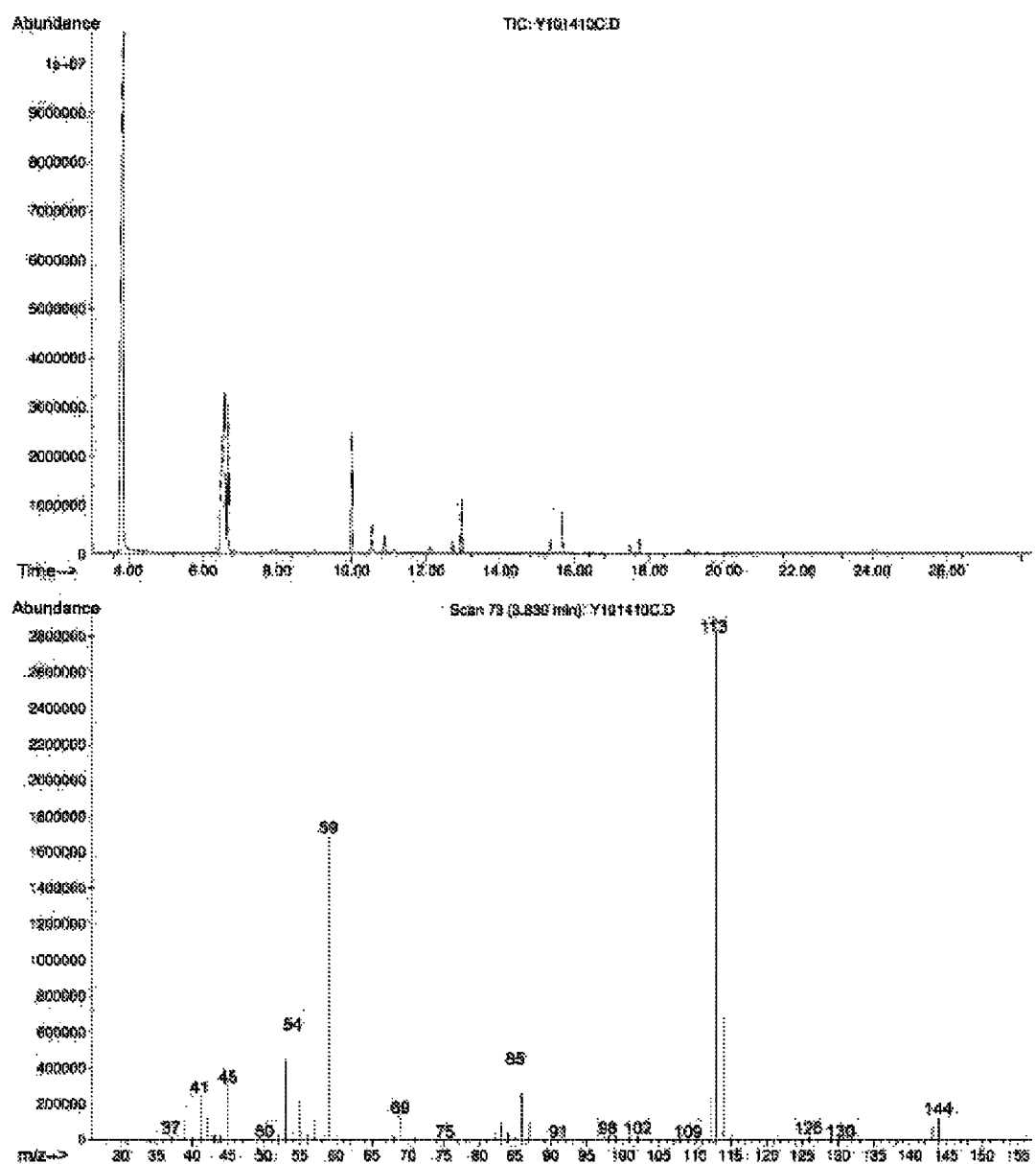
FIG. 12 depicts the depletion of the dimethyl methylene malonate monomer of FIG. 11 over the course of storage at room temperature for 7 days, as depicted by GC-MS.
Figure 13:
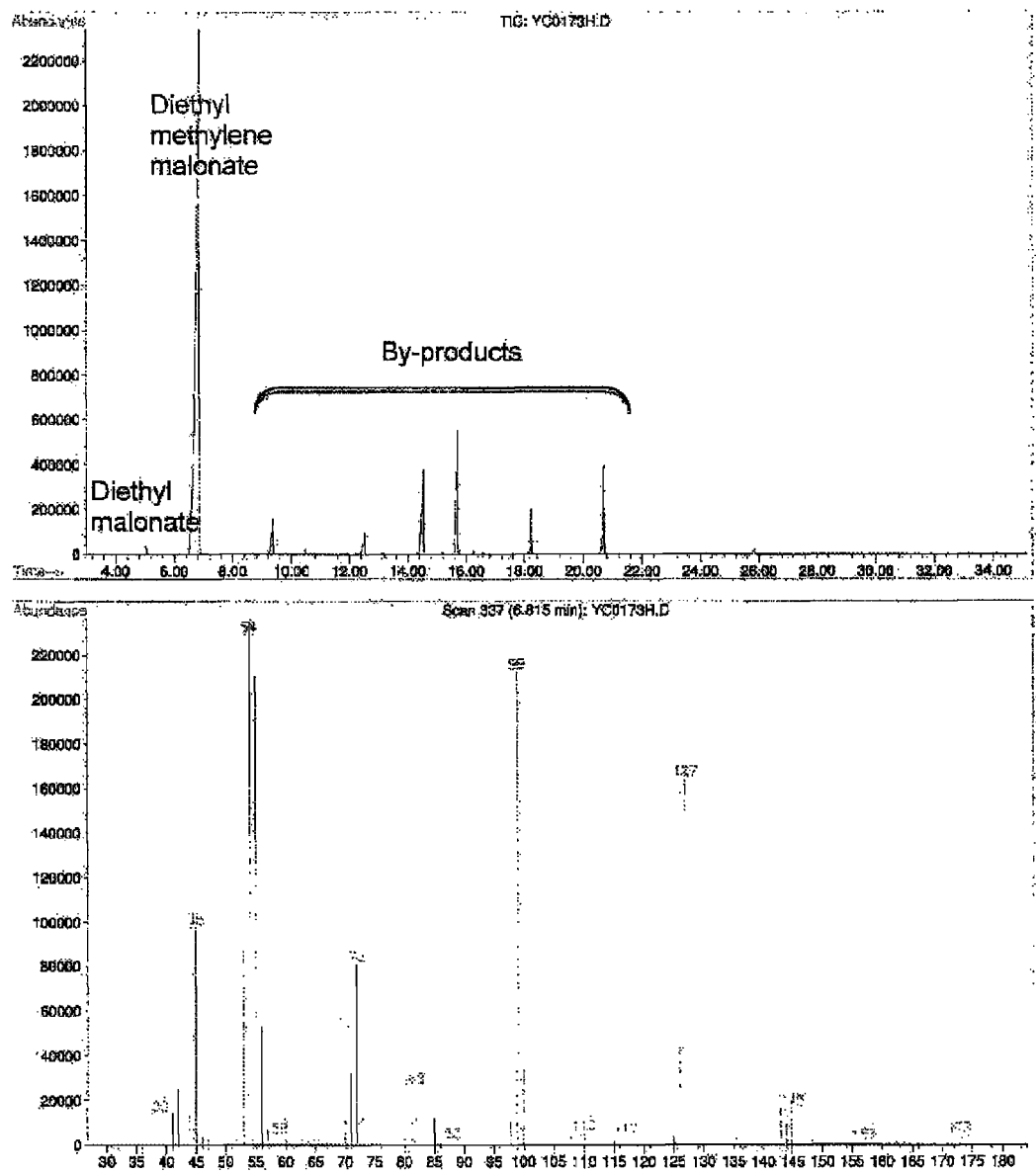
FIG. 13 provides a GC-MS spectrum of a reaction mixture (before distillation).
Figure 14:
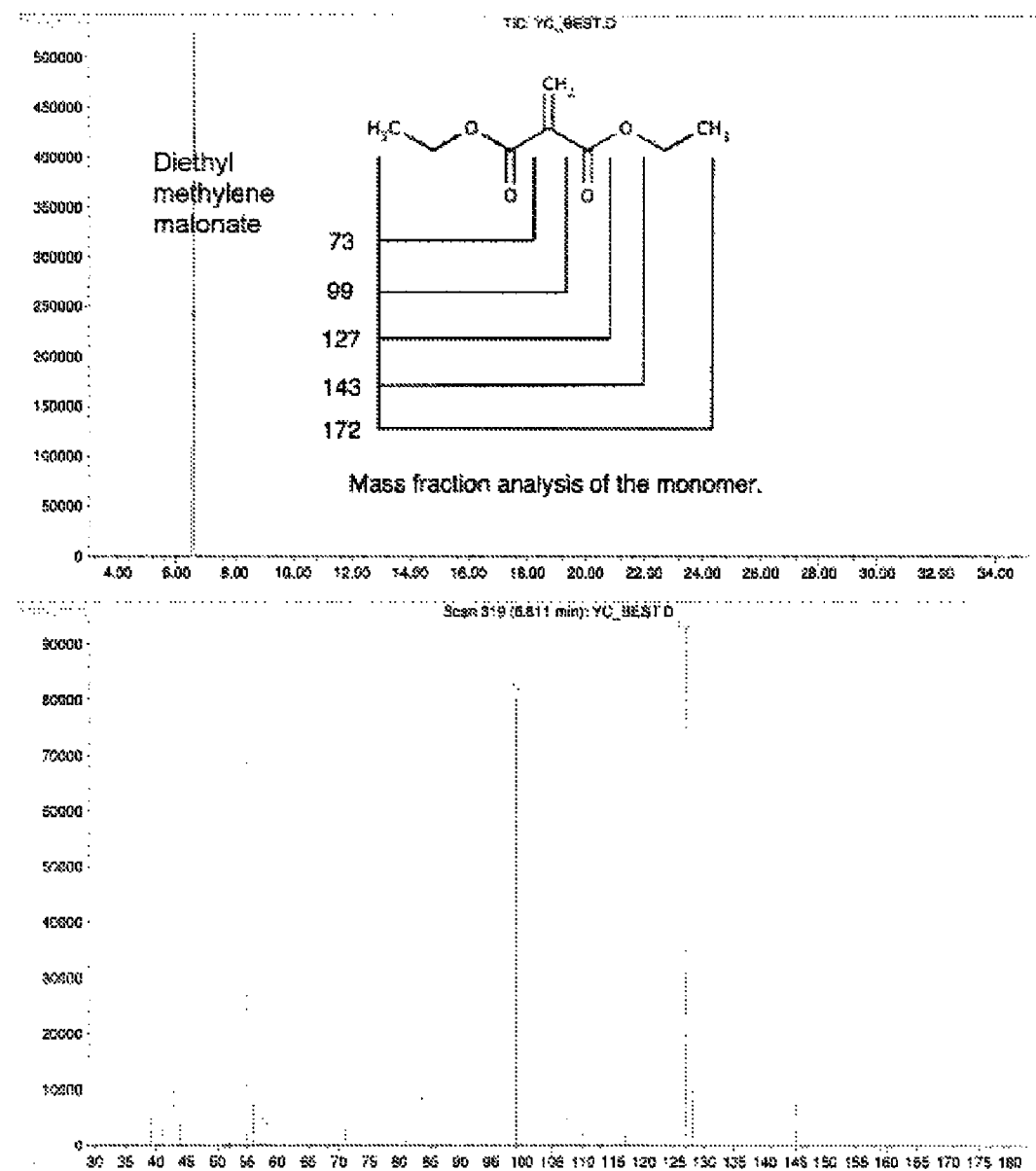
FIG. 14 provides a GC-MS spectrum of a diethyl methylene malonate after second distillation.
Figure 15:
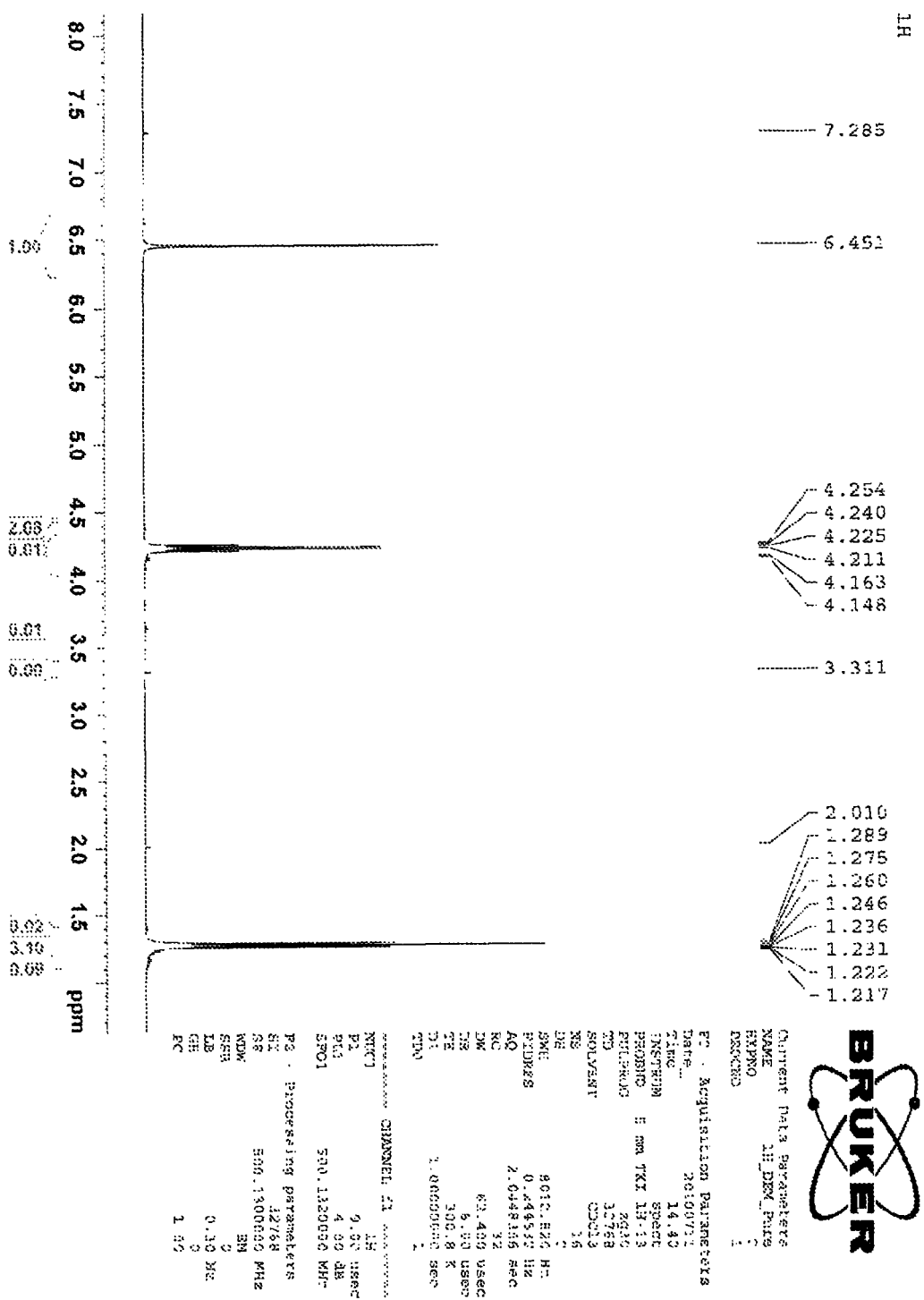
FIG. 15 provides an $^1$HNMR spectrum of diethyl methylene malonate after second distillation.
Figure 16:
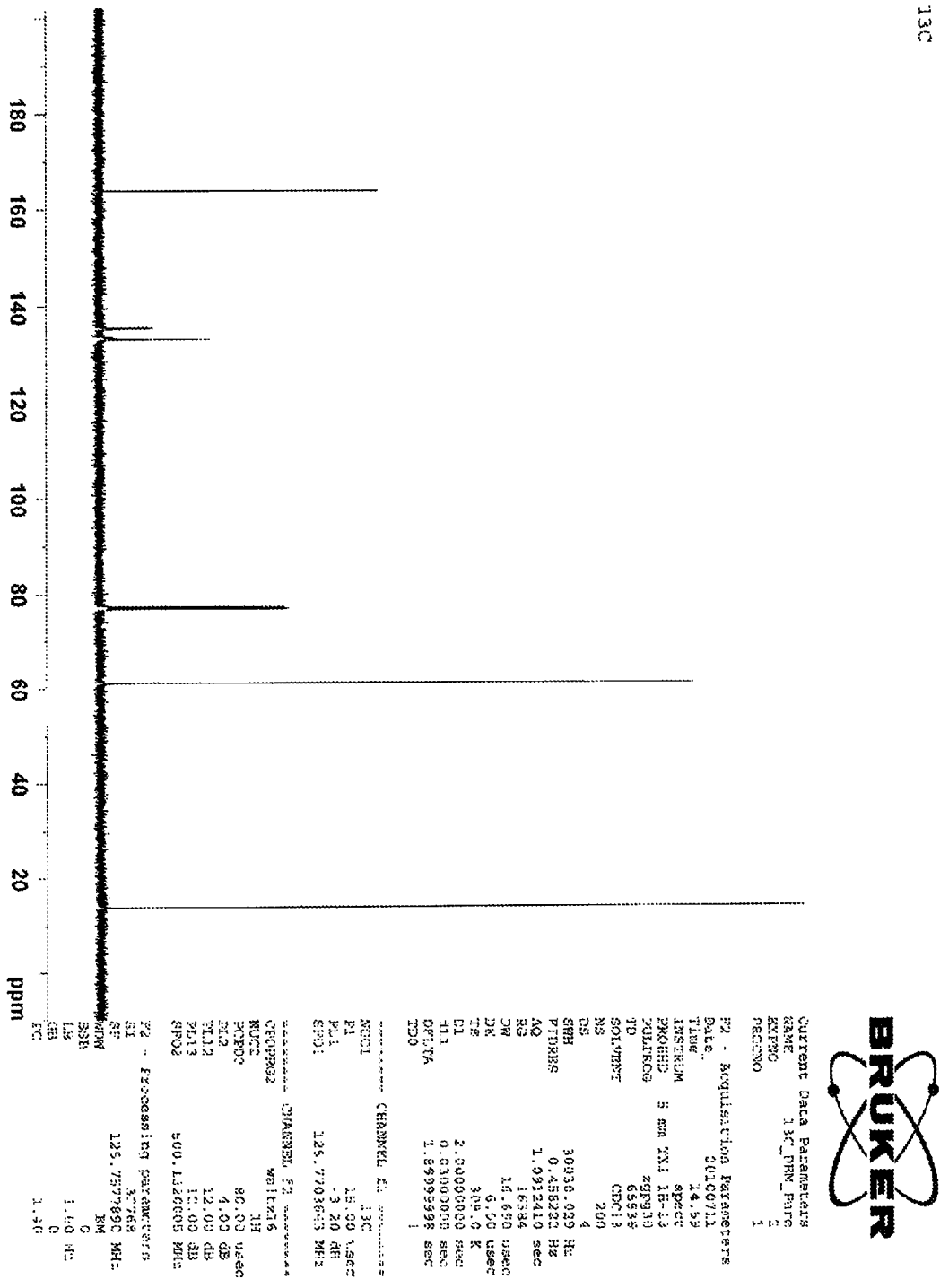
FIG. 16 provides an $^{13}$CNMR spectrum of diethyl methylene malonate after second distillation
Figure 17:
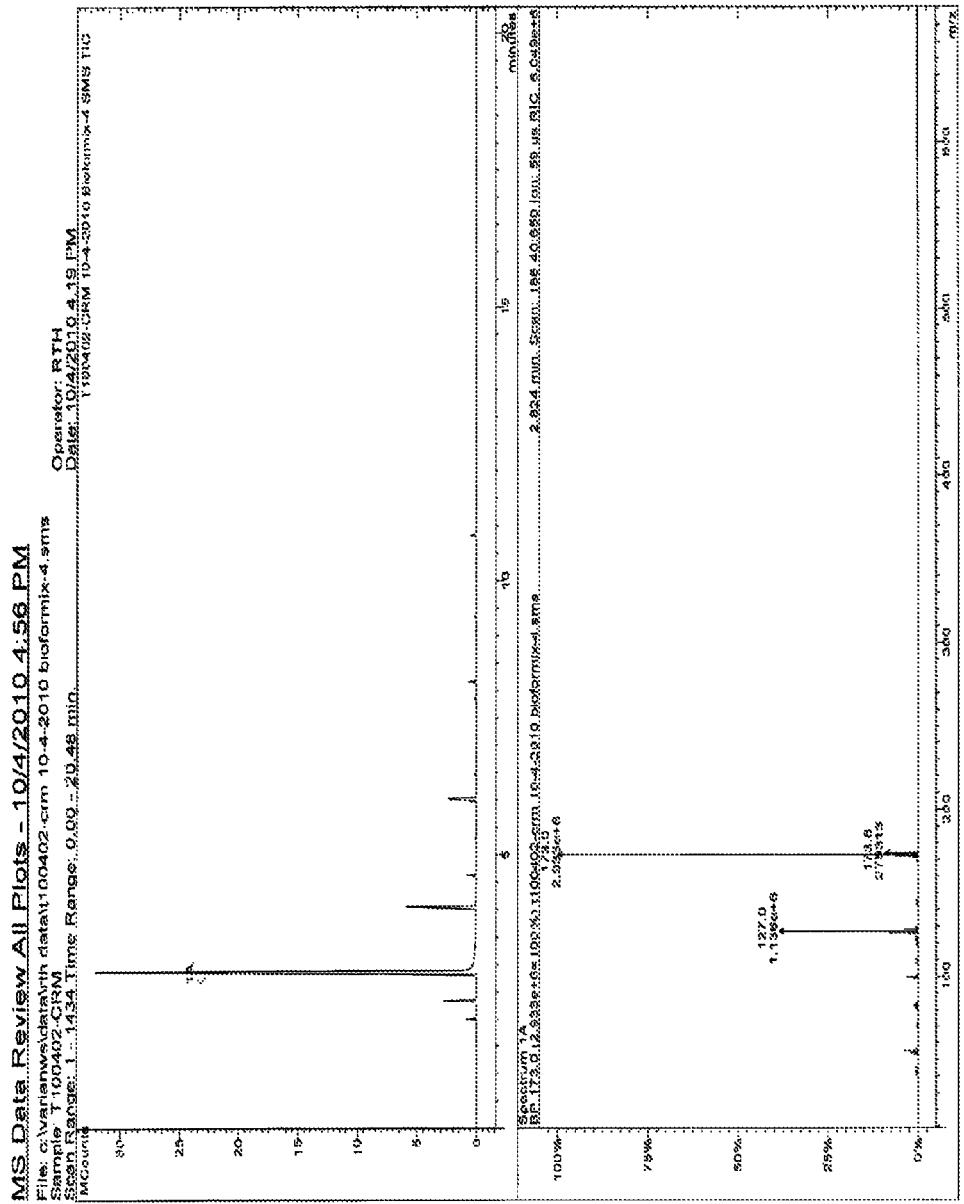
FIG. 17 depicts a GC-MS spectrum of crude diethyl methylene malonate monomer containing water, formaldehyde and other impurities.
Figure 18:
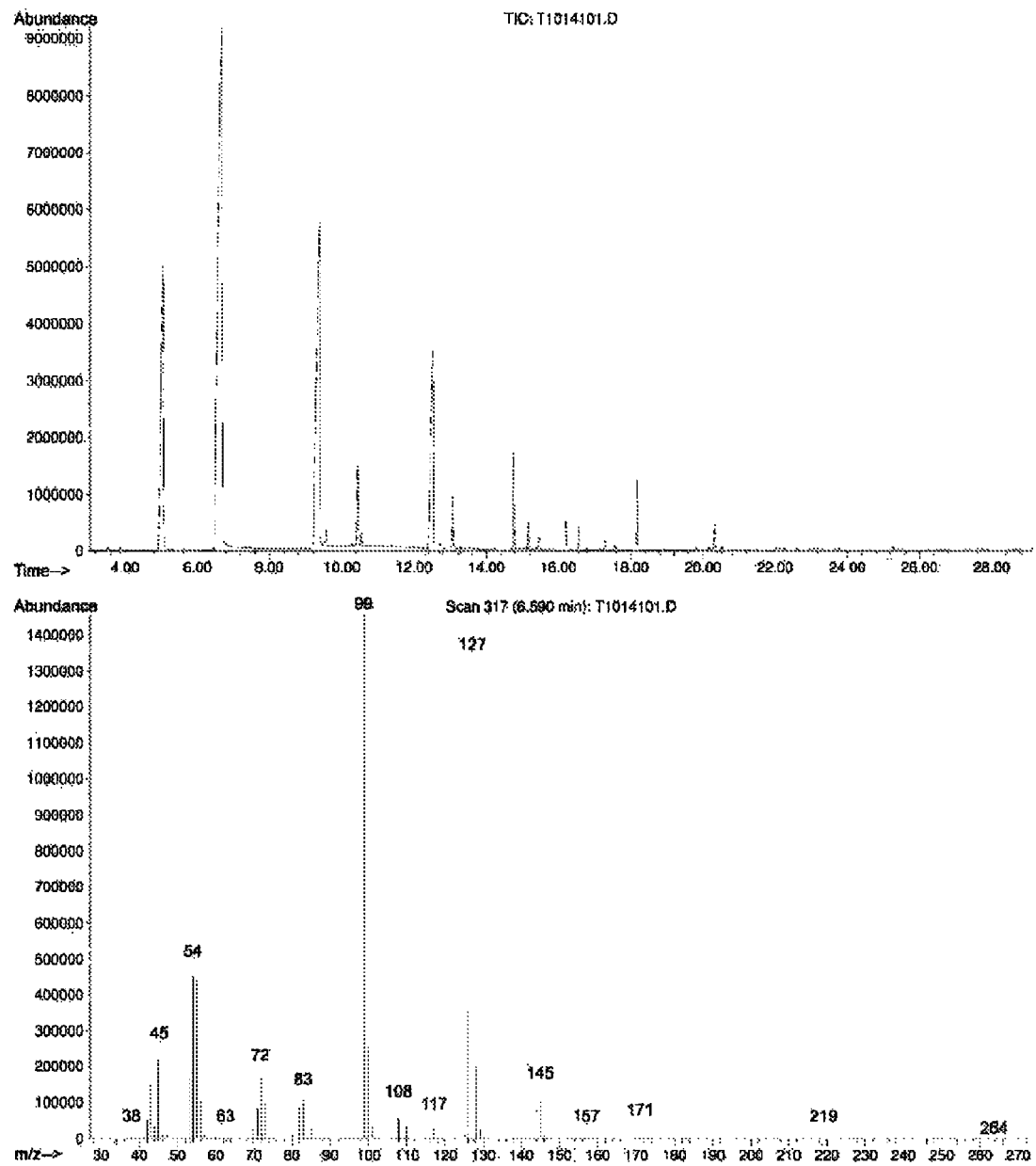
FIG. 18 depicts the depletion of the diethyl methylene malonate monomer of FIG. 17 over the course of storage at room temperature for 7 days, as depicted by GC-MS.
Figure 19:
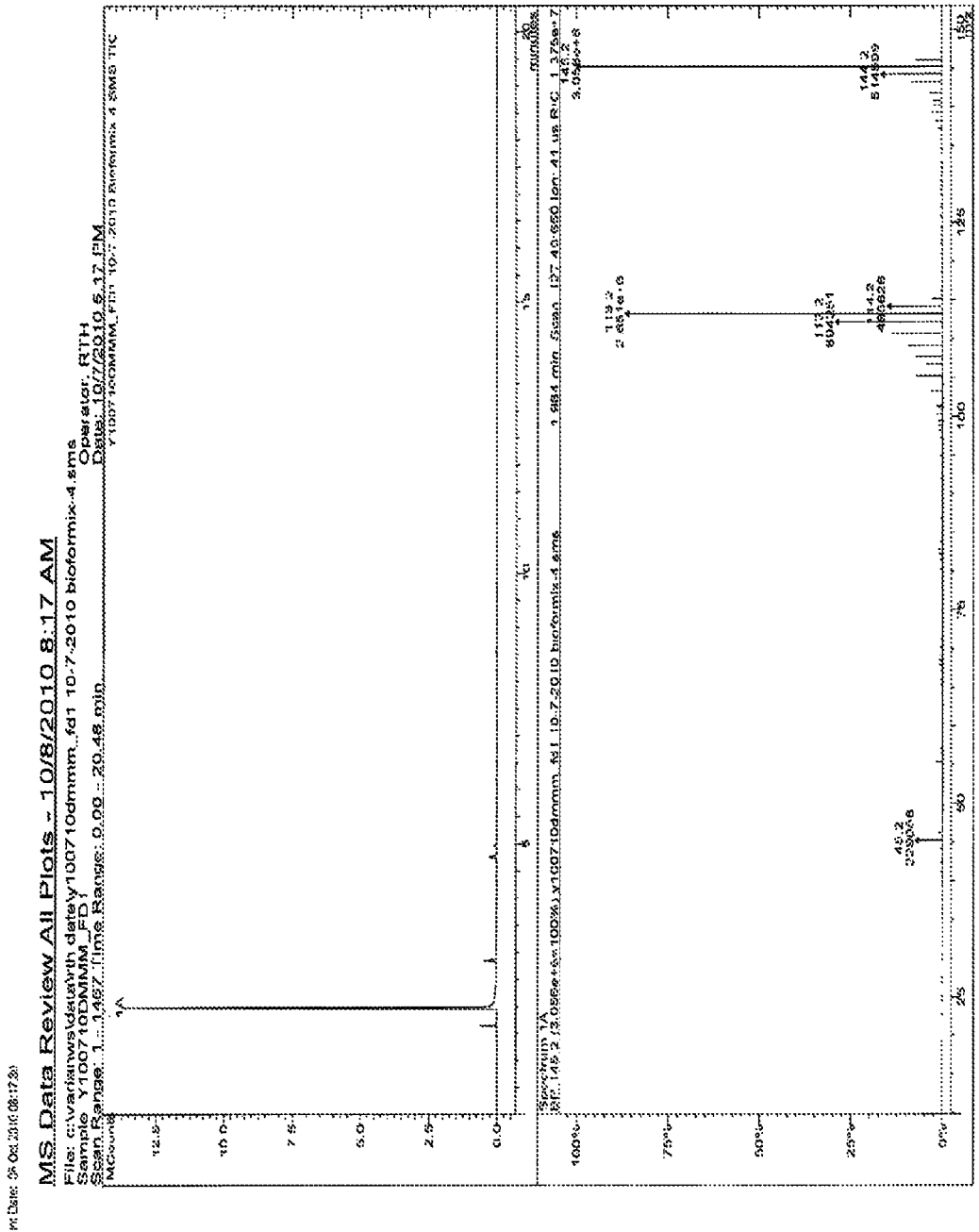
FIG. 19 depicts provides a GC-MS spectrum of crude dimethyl methylene malonate monomer containing water, formaldehyde and other impurities.
Figure 20:
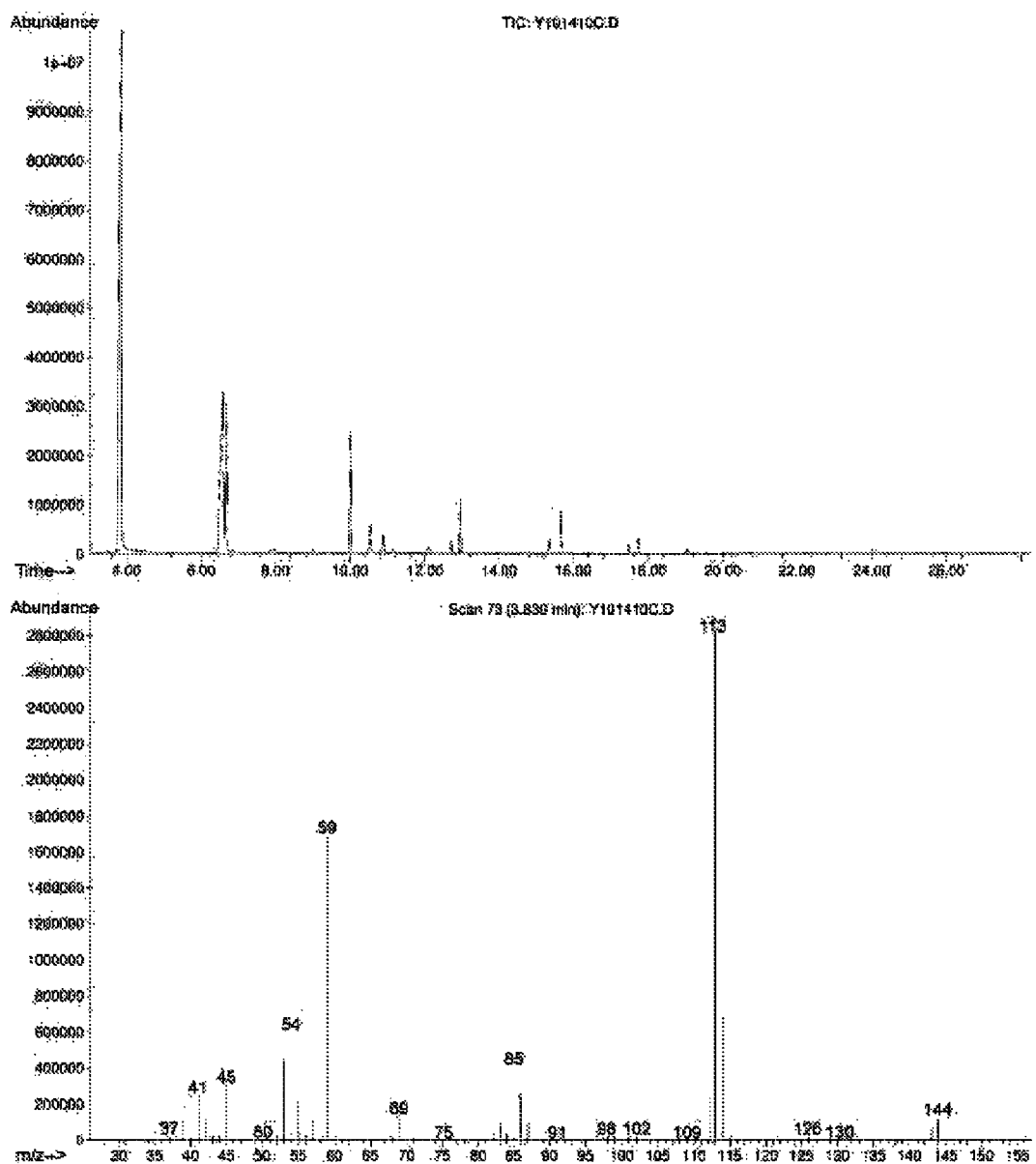
FIG. 20 depicts the depletion of the dimethyl methylene malonate monomer of FIG. 19 over the course of storage at room temperature for 7 days, as depicted by GC-MS.

The spectra presented in FIGS. 11-14 are representative for Batch 2

Example 11

Non-Acidic Solvents with Basic Catalyst with the Dropwise Addition of Diethyl Malonate

1. In a two-liter 3-neck round bottom flask (equipped with a condenser), 30 g of paraformaldehyde (1 mol), 5 g of potassium acetate and 5 g of copper (II) acetate were mixed in 40 ml of tetrahydrofuran (THF).
2. This mixture was stirred and heated at 65° C. for 40 min. From an additional funnel, 80 g (0.5 mol) of diethyl malonate (DEM) was then added dropwise to the reaction mixture.
3. At the end of the addition of DEM (about an hour), the reaction mixture was further stirred at 65° C. for 2 hours.
4. The reaction mixture was then cooled to room temperature and 5 g of sulfuric acid was added into the flask with stirring.
5. The precipitates were then removed by filtration and the filtrate was collected. 0.08 g (1000 ppm) of hydroquinone (HQ) and 0.08 g of sulfuric acid (1000 ppm) were added to the collected filtrate.
6. The filtrate was then distilled at reduced pressure. Diethyl Methylenemalonate was collected at 55-70° C. with about 1.5 mm Hg of vacuum as the crude monomer.
7. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
8. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 12

Non-Acidic Solvents with Basic Catalyst with all Reagents Added all at the Same Time

1. In a two-liter 3-neck round bottom flask (equipped with a condenser), 30 g of paraformaldehyde (1 mol), 80 g (0.5 mol) of diethyl malonate (DEM), 5 g of potassium acetate and 5 g of copper (II) acetate were mixed in 40 ml of tetrahydrofuran (THF).
2 This mixture was stirred and heated at 65° C. for 3 hours.
3. The reaction mixture was then cooled to room temperature and 5 g of sulfuric acid was added into the flask with stirring.
4. The precipitates were then removed by filtration and the filtrate was collected. 0.08 g (1000 ppm) of hydroquinone (HQ) and 0.08 g of sulfuric acid (1000 ppm) were added to the collected filtrate.
5. The filtrate was then distilled at reduced pressure. Diethyl Methylenemalonate was collected at 55-70° C. with about 1.5 mm Hg of vacuum as the crude monomer.
6. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
7 Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 13

Non-Acidic Solvents with Basic Catalyst. Addition of Paraformaldehyde to the Reaction Mixture

1. The 3-neck round bottom flask, with a magnetic stir bar inside, was first dried to make it moisture free, fitted with thermometer and the Dean Stark apparatus connected with a condenser.
2. The reaction solvent, 40 mL of tetrahydrofuran (THF) is then transferred to the RBF. 80 mL of Diethylmalonate (DEM) (0.5 moles), 3 gm of Cu(OAc)$_2$ monohydrate (0.015 moles), 3 gm of Potassium Acetate were all added to the reaction medium sequentially.
3. The initial color of the reaction mixture was blulish-green. The reaction mixture was then heated up to 65 Deg C. for 30 mins.
4. After heating 15 gm of Paraformaldehyde was added over a period of 15 mins. After adding the Paraformaldehyde, N$_2$ gas was bubbled through the reaction mixture to remove the water from the reaction mixture.
5. Removal of water was very crucial because the overall reaction rate slowed down drastically in case of larger scale.
6. The reaction progress was monitored by using GC/MS by taking the aliquot after 1 hr. Based on the unreacted DEM, usually another 10-15 gm of Paraformaldehyde was added for 90-95% conversion of DEM. It was observed that the reaction medium changes color gradually to lighter-bluish green after addition of Paraformaldehyde.
7. After 5.5 hrs of reaction the heating is switched off and once cooled, ~3 gm of H$_2$SO$_4$ was added to the reaction mixture to neutralize the basic catalyst as well as Potassium Acetate.
8. The very light blue color of the reaction mixture indicates the optimum neutralization. After neutralization the salt was the filtered off
9. The filtrate was then set to rotovap under vacuum for evaporating the Toluene/Acetic Acid solvent. Removal of Acetic Acid is crucial because presence of Acetic Acid could increase the curing time of the monomer at parts per million quantities as well as initiate corrosion of metal containing substrates.
10. After that 0.25 g (1000 ppm) of hydroquinone (HQ) and 0.25 g of sulfuric acid (1000 ppm) were added to the collected filtrate.
11. 1$^{st}$ distillation: the filtrate was then distilled at reduced pressure to remove acetic acid. Diethyl Methylenemalonate was collected at 55-70° C. with about 1.5 mm Hg of vacuum as the crude monomer.
12. 2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 14

Non-Acidic Solvents with Acidic Catalyst with the Dropwise Addition of Diethyl Malonate

1. In a two-liter 3-neck round bottom flask (equipped with a condenser), 30 g of paraformaldehyde (1 mol) and 7 g of zinc chloride were mixed in 40 ml of tetrahydrofuran (THF).

2. This mixture was stirred and heated at 65° C. for 40 min. From an additional funnel, 80 g (0.5 mol) of diethyl malonate (DEM) was then added dropwise to the reaction mixture.
3. At the end of the addition of DEM (about an hour), the reaction mixture was further stirred at 65° C. for 2 hours.
4. The reaction mixture was then cooled to room temperature and 7 g of sulfuric acid was added into the flask with stirring.
5. The precipitates were then removed by filtration and the filtrate was collected. 0.08 g (1000 ppm) of hydroquinone (HQ) and 0.08 g of sulfuric acid (1000 ppm) were added to the collected filtrate.
6. The filtrate was then distilled at reduced pressure. Diethyl Methylenemalonate was collected at 55-70° C. with about 1.5 mm Hg of vacuum as the crude monomer.
7. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
8. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 15

Non-Acidic Solvents with Acidic Catalyst. Reagents Added all at the Same Time

1. In a two-liter 3-neck round bottom flask (equipped with a condenser), 80 g (0.5 mol) of diethyl malonate (DEM), 30 g of paraformaldehyde (1 mol) and 7 g of zinc chloride were mixed in 40 ml of tetrahydrofuran (THF).
2 This mixture was stirred and heated at 65° C. for 3 hours.
3. The reaction mixture was then cooled to room temperature and 7 g of sulfuric acid was added into the flask with stirring.
4. The precipitates were then removed by filtration and the filtrate was collected. 0.08 g (1000 ppm) of hydroquinone (HQ) and 0.08 g of sulfuric acid (1000 ppm) were added to the collected filtrate.
5. The filtrate was then distilled at reduced pressure. Diethyl Methylenemalonate was collected at 55-70° C. with about 1.5 mm Hg of vacuum as the crude monomer.
6. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
7 Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 16

Non-Acidic Solvents with Acidic Catalyst. Addition of Paraformaldehyde to the Reaction Mixture The 3-neck RBF, with a magnetic stir bar inside, was first dried to make it moisture free, fitted with thermometer and the Dean Stark apparatus connected with a condenser.

1. 40 ml, of THF, 80 mL of Diethylmalonate (DEM) (0.5 moles) and 3.4 gm of ZnCl2 (0.025 moles) were taken in a 3 neck RBF.
2. The initial color of the reaction mixture was milky white. The reaction mixture was then heated up to 65 Deg C. for 30 mins.
3. After heating 15 gm of paraformaldehyde was added over a period of 15 mins. After adding the paraformaldehyde, N$_2$ gas was bubbled through the reaction mixture to remove the water from the reaction mixture.
4. Removal of water was very crucial because the overall reaction rate slowed down drastically in case of larger scale.
5. The reaction progress was monitored by using GC/MS by taking the aliquot after 1 hr. Based on the unreacted DEM, usually another 5-10 gm of Paraformaldehyde was added for 90-95% conversion of DEM.
6. After 5.5 hrs of reaction the heating is switched off and once cooled, ~3 gm of H$_2$SO$_4$ was added to the reaction mixture to neutralize the basic catalyst as well as Potassium Acetate.
7. The transparent reaction mixture indicates the optimum neutralization. After neutralization the salt was the filtered off.
8. The filtrate was then set to rotovap under vacuum for evaporating the Toluene/Acetic Acid solvent. Removal of Acetic Acid was crucial because presence of Acetic Acid could increase the curing time of the monomer even though the GC is showing 98-99% purity.
9. After that 0.25 g (1000 ppm) of hydroquinone (HQ) and 0.25 g of sulfuric acid (1000 ppm) were added to the collected filtrate.
10. 1$^{st}$ distillation: the filtrate was then distilled at reduced pressure to remove acetic acid. Diethyl Methylenemalonate was collected at 55-70° C. with about 1.5 mm Hg of vacuum as the crude monomer.
11. 2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 17

Solventless with Basic Catalyst

1. To a 3-neck, round bottom flask equipped with thermocouple, mechanical stirrer, and nitrogen blanket, is charged 120 g (0.75 moles) of diethylmalonate (DEM).
2. With stirring, 45 g (1.5 moles) of paraformaldehyde was added. In addition, the catalyst system consists of 1 gm (0.73 mol %) of copper (II) acetate with 2 gms (2.7 mol %) of potassium acetate, based on DEM, was lastly added.
3. The reaction mixture was heated slowly to ~60° C. whereby an exotherm to 110-115 C occurs.
4. The temperature of the resulting reaction mixture was maintained at 85° C. for 30 minutes.
5. The reaction mixture was then filtered through silica plug to remove catalysts and the filtrate was collected.
6. The filtrate was stabilized by sulfuric acid and hydroquinone.

7.7. The filtrate was then distilled at reduced pressure. Diethyl Methylenemalonate was collected at 55-70° C. with about 1.5 mm Hg of vacuum as the crude monomer.
8. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
9 Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 18

Solventless with Acidic Catalyst. Reagents Added all at the Same Time

1. In a two-liter 3-neck round bottom flask (equipped with a condenser), 80 g (0.5 mol) of diethyl malonate (DEM), 30 g of paraformaldehyde (1 mol) and 7 g of zinc chloride were mixed together.
2 This mixture was stirred and heated at 65° C. for 1 hour.
3. The reaction mixture was then cooled to room temperature and 7 g of sulfuric acid was added into the flask with stirring.
4. The precipitates were then removed by filtration and the filtrate was collected. 0.08 g (1000 ppm) of hydroquinone (HQ) and 0.08 g of sulfuric acid (1000 ppm) were added to the collected filtrate.
5. The filtrate was then distilled at reduced pressure. Diethyl Methylenemalonate was collected at 55-70° C. with about 1.5 mm Hg of vacuum as the crude monomer.
6. The crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum.
7 Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 19

Solventless with Acidic Catalyst. Addition of Paraformaldehyde to the Reaction Mixture The 3-neck RBF, with a magnetic stir bar inside, was first dried to make it moisture free, fitted with thermometer and the Dean Stark apparatus connected with a condenser.
1. 80 mL of Diethylmalonate (DEM) (0.5 moles) and 3.4 gm of ZnCl2 (0.025 moles) were taken in a 3 neck RBF.
2. The initial color of the reaction mixture was milky white. The reaction mixture was then heated up to 65 Deg C. for 30 mins.
3. After heating 15 gm of paraformaldehyde was added over a period of 15 mins. After adding the paraformaldehyde, N$_2$ gas was bubbled through the reaction mixture to remove the water from the reaction mixture.
4 Removal of water was very crucial because the overall reaction rate slowed down drastically in case of larger scale.
5. The reaction progress was monitored by using GC/MS by taking the aliquot after 1 hr. Based on the unreacted DEM, usually another 5-10 gm of Paraformaldehyde was added for 90-95% conversion of DEM.
6. After 5.5 hrs of reaction the heating is switched off and once cooled, ~3 gm of H$_2$SO$_4$ was added to the reaction mixture to neutralize the basic catalyst as well as Potassium Acetate.
7. The transparent reaction mixture indicates the optimum neutralization. After neutralization the salt was the filtered off.
8. The filtrate was then set to rotovap under vacuum for evaporating the Toluene/Acetic Acid solvent. Removal of Acetic Acid was crucial because presence of Acetic Acid could increase the curing time of the monomer even though the GC is showing 98-99% purity.
9. After that 0.25 g (1000 ppm) of hydroquinone (HQ) and 0.25 g of sulfuric acid (1000 ppm) were added to the collected filtrate.
10. 1$^{st}$ distillation: the filtrate was then distilled at reduced pressure to remove acetic acid. Diethyl Methylenemalonate was collected at 55-70° C. with about 1.5 mm Hg of vacuum as the crude monomer.
11. 2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10-50 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 20

Acetic Acid Solvent with Basic Catalyst

In a two-liter 3-neck round bottom flask (equipped with a condenser, thermal couple and additional funnel), 30 g of paraformaldehyde (1 mol), 5 g of potassium acetate and 5 g of copper (II) acetate were mixed in 200 ml of acetic acid. This mixture was stirred and heated at 85° C. for 40 min. From additional funnel, 80 g (0.5 mol) of diethyl malonate (DEM) was then added drop-wise to the reaction mixture. At the end of the addition of DEM (about an hour), the reaction mixture was further stirred at 85° C. for 2 hours.

The reaction mixture was then cooled to room temperature and 5 g of sulfuric acid was added into the flask with stirring. The precipitates were then removed by filtration and the filtrate was collected. 0.25 g (1000 ppm) of hydroquinone (HQ) and 0.25 g of sulfuric acid (1000 ppm) were added to the collected filtrate.

Purification of Monomer

1$^{st}$ distillation: the filtrate was then distilled at reduced pressure to remove acetic acid. Diethyl Methylenemalonate was collected at 55-70° C. with about 1.5 mm Hg of vacuum as the crude monomer.

2$^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Example 21

Acetic Acid Solvent with Acidic Catalyst

In a two-liter 3-neck round bottom flask (equipped with a condenser, thermal couple and additional funnel), 30 g of paraformaldehyde (1 mot) and 6.8 g of zinc chloride were mixed in 200 ml of acetic acid. This mixture was stirred and heated at 85° C. for 40 min. From additional funnel, 80 g (0.5 mol) of diethyl malonate (DEM) was then added drop-wise to the reaction mixture. At the end of the addition of DEM (about an hour), the reaction mixture was further stirred at 85° C. for 2 hours.

The reaction mixture was then cooled to room temperature and 5 g of sulfuric acid was added into the flask with stirring. The precipitates were then removed by filtration and the filtrate was collected. 0.25 g (1000 ppm) of hydroquinone (HQ) and 0.25 g of sulfuric acid (1000 ppm) were added to the collected filtrate.

Purification of Monomer $1^{st}$ distillation: the filtrate was then distilled at reduced pressure to remove acetic acid. Diethyl Methylenemalonate was collected at 55-70° C. with about 1.5 mm Hg of vacuum as the crude monomer.

$2^{nd}$ distillation: the crude monomer (with 1000 ppm of HQ and 1000 ppm of sulfuric acid) was further fractionally distilled with stainless steel packed column under reduced vacuum. Pure monomer was collected at 55° C. with 1.1 mm Hg of vacuum. Monomer was stabilized with 1000 ppm of HQ and 10 ppm of chlorodifluoroacetic acid.

$^1$H-NMR (400 MHz, CDCl$_3$) δ 6.45 (s, 2H), 4.22 (q, 4H), 1.24 (t, 6H). GC-MS (m/z): 172, 145, 127, 99, 55.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES CITES

The following documents may be cited or referenced herein, each of which are incorporated by reference herein and may be employed in the practice of the invention.

Such documents may include the following patents: U.S. Pat. Nos. 2,313,501; 2,330,033; 3,197,318; 3,221,745; 3,523,097; 3,557,185; 3,758,550; 3,975,422; 4,049,698; 4,056,543; 4,160,864; 4,931,584; 5,142,098; 5,550,172; 6,106,807; 6,211,273; 6,245,933; 6,420,468; 6,440,461; 6,512,023; 6,610,078; 6,699,928; 6,750,298; and 2004/0076601.

Such documents may also include the following non-patent literature:

M. Ware et al.: "DBU: An Efficient Catalyst for Knoeveganel Condensation under Solvent-free Condition," Bulletin of the Catalysis Society of India, (2007), Vol. 6, pp. 104-106;

V. G. Nenajdenko et al.: "Reaction of 2-Methylene-1,3-Dicarbonyl Compounds Containing a CF$_3$-Group with 1,3-Dienes," Tetrahedron, (2000), Vol. 56, pp. 6549-6556;

J. S. Yadav et al.: "Phosphate-Catalyzed Knoevenagel Condensation: a Facile Synthesis of α-Cyanoacrylates and α-Cyanoacrylonitriles," Eur. J. Org. Chem. (2004), pp. 546-551;

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org. Chem., (2006), pp. 3767-3770;

H. A. Oskooie et al.: "On Water: an Efficient Knoevenagel Condensation using 12-Tungstophosphoric Acid as a Reusable Green Catalyst," Synthetic Communications, (2006), Vol. 36, pp. 2819-2823;

H. Jiang et al.: "Inorganic Zinc Salts Catalyzed Knoevenagel Condensation at Room Temperature without Solvent," Preparative Biochemistry & Biotechnology, (2009), Vol. 39, pp. 194-200;

B. M. Reddy et al.: "An Easy-to-use Heterogeneous Promoted Zirconia Catalyst for Knoevenagel Condensation in liquid Phase under Solvent-Free Conditions," Journal of Molecular Catalysis A: Chemical, (2006), Vol. 258, pp. 302-307;

D. H. Jung et al.: "New and General Methods for the Synthesis of Arylmethylene Bis(3-Hydroxy-2-Cyclohexene-1-Ones) and Xanthenediones by EDDA and In(OTf)$_3$-Catalyzed One-Pot Domino Knoevenagel/Michael or Koevenagel/Michael/Cyclodehydration Reactions," Bull. Korean Chem. Soc. (2009) Vol. 30, No. 9, pp. 1989-1995;

P. Klemarczyk: "Adhesion Studies of Mixtures of Ethyl Cyanoacrylate with a Difunctional Cyanoacrylate Monomer and with other Electron-deficient Olefins," J. Adhesion, (1999), Vol. 69, pp. 293-306;

P. Klemarwczyk: "A General Synthesis of 1,1 Disubstituted Electron Deficient Olefins and their Polymer Properties," Polymer, (1998), Vol. 39, No. 1, pp. 173-181;

C. Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Aurangabad 431 004 (MS), India, (n/a), pp. n/a;

P. Ballesteros et al.: "DI-tert-Butyl Methylenemalonate [Propanedioic Acid, Methylene-, bis(1,1-dimethylethyl)ester]," Organic Syntheses. Coll. (1990), Vol. 7, p. 142; (1986) Vol. 64, p. 63;

A. M. Vetrova et al.: "Improvement of the Thermal Stability of Cyanoacrylate Adhesives," Polymer Science, Series D, (2009), Vol. 2, No. 1, pp. 27-30;

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), Vol. 59, pp. 2327-2330;

G. Lai et al.: "Ionic Liquid Functionalized Silica Gel: Novel Catalyst and Fixed Solvent," Tetrahedron Letters (2006), Vol. 47, pp. 6951-6953;

J. R. Harjani et al.: "Lewis Acidic Ionic Liquids for the Synthesis of Electrophilic Alkenes via the Knoevenagel Condensation," Tetrahedron Letters, (2002), Vol. 43, pp. 1127-1130;

P. Ballesteros et al.: "Synthesis of DI-tert-Butyl Methylenemalonate, a Sterically Hindered 1,1-Dicarbonyl Alkene," J. Org. Chem, (1983), Vol. 48, pp. 3603-3605; and T. Doi et al.: "Synthesis of Dimethyl gloiosiphne A by Way of Palladium-Catalyzed Domino Cyclization," J. Org. Chem., (2007), Vol. 72, pp. 3667-3671.

What is claimed is:

1. A method of making a methylene malonate monomer comprising: (a) reacting a malonic acid ester with a source of formaldehyde in the presence of an acidic or basic catalyst and in the absence of a solvent, to form a reaction complex; (b) optionally, inactivating the catalyst; and (c) recovering methylene malonate monomer from the reaction complex.

2. The method according to claim 1, wherein inactivating the catalyst comprises forming an insoluble precipitate of the catalyst and removing the precipitate from the reaction mixture.

3. The method according to claim 2, wherein the precipitate is formed by reducing the solubility of the catalyst in the reaction mixture.

4. The method according to claim 1 further comprising:
   (d) minimizing the recovery of volatile latent acid forming impurities from the reaction complex.

5. The method according to claim 4, wherein the step of minimizing the recovery of volatile latent acid forming impurities comprises:
   (a) adding to the reaction mixture water and an acid having a pKa range of −8 to 5;
   (b) adding to the reaction mixture a sterically hindered organic acid; or
   (c) adding to the reaction mixture a non-volatile organic acid, or any combination of (a), (b) or (c).

6. The method according to claim 1 comprising the basic catalyst, wherein the basic catalyst is selected from the group consisting of potassium acetate, sodium acetate, zinc acetate, aluminum acetate, calcium acetate, magnesium acetate, magnesium oxide, copper acetate, lithium acetate, aluminum oxide and zinc oxide, and combinations thereof.

7. The method according to claim 1 comprising the acidic catalyst, wherein the acidic catalyst is selected from the group consisting of paratoluene sulfonic acid, dodecylbenzene sulfonic acid, boron trifluoride, zinc perchlorate, sulfated zirconium oxide, sulfated titanium oxide, lithium chloride, boron trifluoride etherate, ferric sulfate, zirconium oxychloride, cupric chloride, titanium tetrachloride and zinc chloride.

8. The method according to claim 1, wherein the recovering step comprises at least one process selected from the group consisting of condensation, simple distillation, fractional distillation, flash distillation, steam distillation, vacuum distillation, short path distillation, thin-film distillation, reactive distillation, pervaporation, extractive evaporation, flash evaporation, and rotary evaporation.

9. The method according to claim 1, wherein the recovering step is performed at reduced pressure.

10. The method according to claim 1, wherein the malonic acid ester has the formula:

$$R-O-C(O)-CH2-C(O)-O-R'$$

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl-($C_1$-$C_{15}$ alkyl), heteroaryl or heteroaryl-($C_1$-$C_{15}$ alkyl), or alkoxy-($C_1$-$C_{15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; or wherein R and R' are taken together with the atoms to which they are bound to form a 5-7 membered heterocyclic ring which may be optionally substituted by $C_1$-$C_{15}$ alkyl, halo-$C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

\* \* \* \* \*